United States Patent [19]

Takasugi et al.

[11] Patent Number: 5,622,976
[45] Date of Patent: Apr. 22, 1997

[54] OXADIAZOLE DERIVATIVES HAVING ACETYLCHOLINESTERASE-INHIBITORY AND MUSCARINIC AGONIST ACTIVITY

[75] Inventors: Hisashi Takasugi, Sakai; Atsushi Kuno, Osaka; Mitsuru Ohkubo, Hyogo, all of Japan

[73] Assignee: Fujisawa Pharmaceutical Co., Ltd., Osaka, Japan

[21] Appl. No.: 244,904

[22] PCT Filed: Dec. 18, 1992

[86] PCT No.: PCT/JP92/01658

§ 371 Date: Jun. 24, 1994

§ 102(e) Date: Jun. 24, 1994

[87] PCT Pub. No.: WO93/13083

PCT Pub. Date: Jul. 8, 1993

[30]  Foreign Application Priority Data

Dec. 31, 1991 [GB] United Kingdom .................. 9127533
Oct. 5, 1992 [GB] United Kingdom .................. 9220904

[51] Int. Cl.⁶ ..................... A61K 31/445; C07D 413/12
[52] U.S. Cl. .......................... 514/326; 514/305; 514/340; 546/135; 546/138; 546/210; 546/269.1
[58] Field of Search .................... 546/135, 138, 546/210, 277; 514/305, 326, 340

[56] References Cited

U.S. PATENT DOCUMENTS

| | | | |
|---|---|---|---|
| 4,699,913 | 10/1987 | Farooq et al. | 514/333 |
| 4,933,353 | 6/1990 | Jensen et al. | 514/340 |
| 5,041,456 | 8/1991 | Baker et al. | 514/361 |
| 5,091,397 | 2/1992 | Wadsworth et al. | 514/359 |
| 5,134,146 | 7/1992 | Showell et al. | 514/299 |
| 5,328,923 | 7/1994 | Sauerberg et al. | 514/340 |

FOREIGN PATENT DOCUMENTS

| | | |
|---|---|---|
| 239309 | 9/1987 | European Pat. Off. |
| 316718 | 5/1989 | European Pat. Off. |
| 323864 | 7/1989 | European Pat. Off. |
| 1481025 | 12/1962 | France |

OTHER PUBLICATIONS

Street et al. "Synthesis and biological activity of 1,2,4–oxadiazole derivatives", J. Med. Chem. v33 pp. 2690–2697 (1990).

Imai et al. "Biological studies of AT–308" Atherosclerosis v17 pp. 121–129 (1973).

*Primary Examiner*—Ceila Chang
*Attorney, Agent, or Firm*—Oblon, Spivak, McClelland, Maier & Neustadt, P.C.

[57]  ABSTRACT

Heterocyclic compounds of the formula:

$$R^1-Q-Z-X-A-M$$

wherein $R^1$ is lower alkyl, a heterocyclic group which may have suitable substituent(s), etc;

Q is oxadiazolediyl,

Z is bond or vinyl,

X is bond,
a group of the formula:

$$-\overset{R^4}{\underset{|}{\text{CON}}}-$$

(in which $R^4$ is hydrogen or lower alkyl), a group of the formula:

$$-\overset{R^8}{\underset{|}{\text{CH}}}-$$

(in which $R^8$ is hydroxy or protected hydroxy), etc;

A is bond, lower alkylene or lower alkynylene and

M is a heterocyclic group containing at least one nitrogen atom which may have one substituent selected from the group consisting of lower alkyl, an imino protective group and ar(lower)alkyl which may have suitable substituent(s), and a pharmaceutically acceptable salt thereof which are useful as a medicament.

7 Claims, No Drawings

OXADIAZOLE DERIVATIVES HAVING ACETYLCHOLINESTERASE-INHIBITORY AND MUSCARINIC AGONIST ACTIVITY

This application is a 371 of PCT/JP92/01658 filed Dec. 18, 1992.

TECHNICAL FIELD

This invention relates to and pharmaceutically acceptable salts thereof which are useful as a medicament.

DISCLOSURE OF INVENTION

This invention relates to new heterocyclic compounds. More particularly, this invention relates to new oxadiazole derivatives and pharmaceutically acceptable salts thereof which have pharmacological activities, processes for preparation thereof, a pharmaceutical composition comprising the same and a use of the same.

Accordingly, one object of this invention is to provide the new and useful oxadiazole derivatives and pharmaceutically acceptable salts thereof which possess an acetylcholinesterase-inhibitory activity and muscarinic agonist activity.

Another object of this invention is to provide processes for preparation of the oxadiazole derivatives and their salts thereof.

A further object of this invention is to provide a pharmaceutical composition comprising said oxadiazole derivatives or a pharmaceutically acceptable salt thereof.

Still further object of this invention is to provide a use of said oxadiazole derivative or a pharmaceutically acceptable salt thereof as a medicament for prophylactic and therapeutic treatment of disorders in the central nervous system such as amnesia, dementia [e.g. senile dementia of Alzheimer type, vascular dementia etc.], cerebrovascular disease, in human being and animals.

The object oxadiazole derivatives of the present invention are novel and represented by the following general formula (I):

$$R^1-Q-Z-X-A-M \quad (I)$$

wherein
  $R^1$ is lower alkyl, a heterocyclic group which may have suitable substituent(s), aryl which may have suitable substituent(s), ar(lower)alkyl which may have suitable substituent(s), or ar(lower)alkenyl which may have suitable substituent(s),
  Q is oxadiazolediyl,
  Z is bond or vinyl,
  X is bond,
    a group of the formula:

$$\begin{array}{c} R^4 \\ | \\ -CON- \end{array}$$

(in which $R^4$ is hydrogen or lower alkyl), a group of the formula:

$$\begin{array}{c} R^8 \\ | \\ -CH- \end{array}$$

(in which $R^8$ is hydroxy or protected hydroxy),

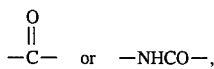

A is bond, lower alkylene or lower alkynylene and

M is a heterocyclic group containing at least one nitrogen atom which may have one substituent selected from the group consisting of lower alkyl, an imino protective group and ar(lower)alkyl which may have suitable substituent(s).

The object compound (I) of the present invention can be prepared by the following processes.

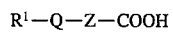
Process (1)

$$R^1-Q-Z-COOH$$

(II)
or its reactive derivative
at the carboxy group,
or a salt thereof $$\Big| \begin{array}{l} H_2N-A-M \\ \text{(III)} \\ \text{or its reactive derivative} \\ \text{at the amino group,} \\ \text{or a salt thereof} \end{array}$$

$$\downarrow$$

$$R^1-Q-Z-CONH-A-M$$

(Ia)
or a salt thereof

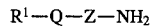
Process (2)

$$R^1-Q-Z-NH_2$$

(IV)
or its reactive derivative
at the amino group,
or a salt thereof $$\Big| \begin{array}{l} \text{O} \\ \| \\ HO-C-A-M \\ \text{(V)} \\ \text{or its reactive derivative} \\ \text{at the carboxy group,} \\ \text{or a salt thereof} \end{array}$$

$$\downarrow$$

$$R^1-Q-Z-NHCO-A-M$$

(Ib)
or a salt thereof

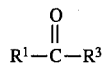
Process (3)

$$\begin{array}{c} O \\ \| \\ R^1-C-R^3 \end{array}$$

(VI)
or a salt thereof $$\Big| \begin{array}{l} N\sim OH \\ \| \\ H_2N-C-Z-X-A-M \\ \text{(VII)} \\ \text{or a salt thereof} \end{array}$$

$$\downarrow$$

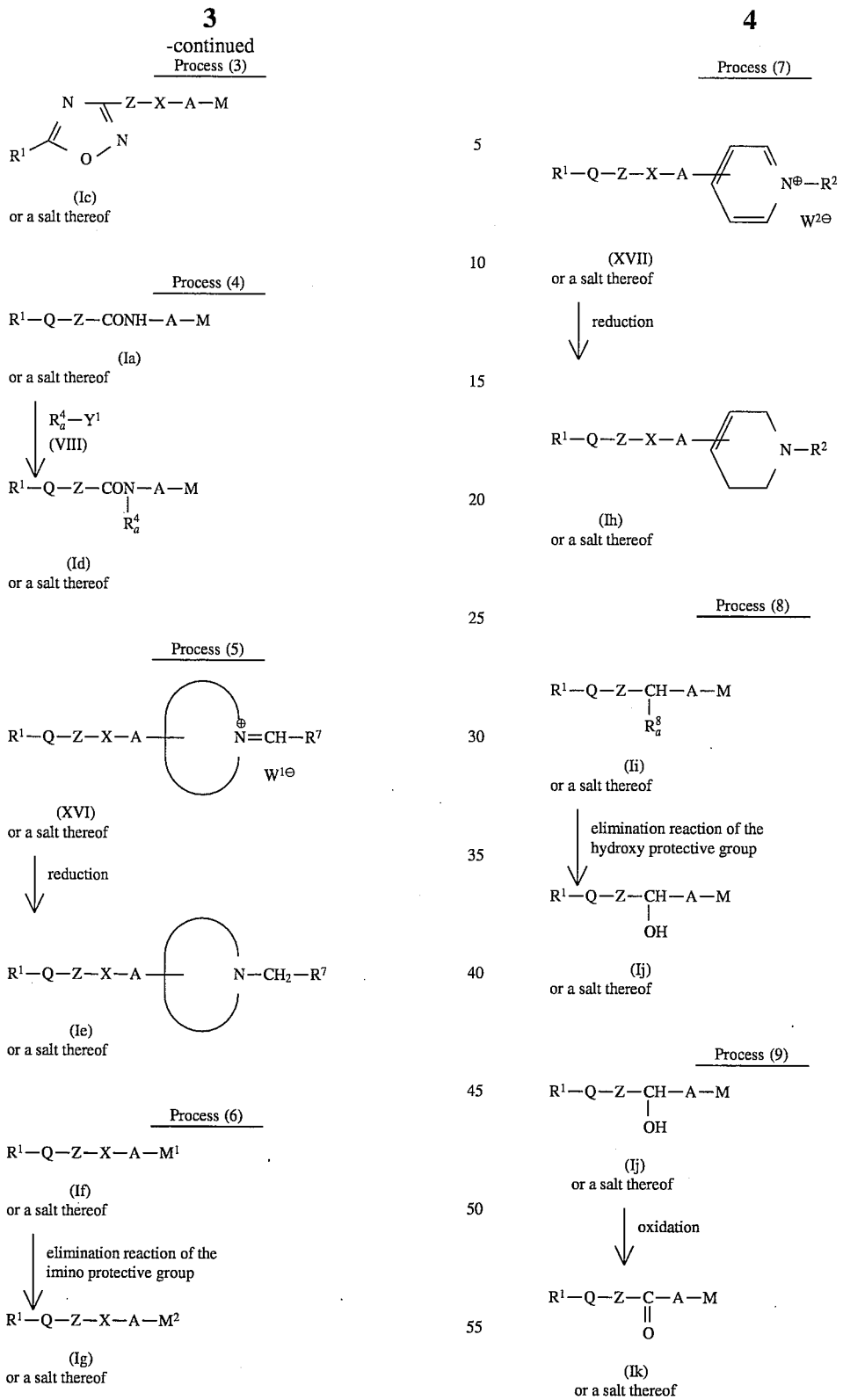

Process (10)

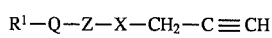

(XXV)
or a salt thereof

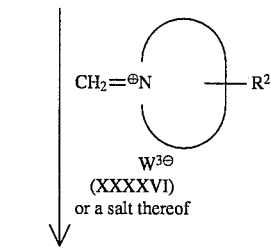

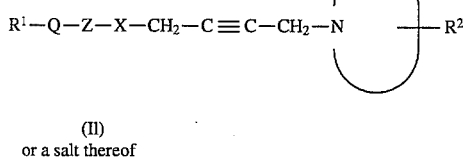

(II)
or a salt thereof wherein
  $R^1$, Q, Z, A, X and M are each as defined above,
  $R^2$ is lower alkyl, an imino protective group, or ar(lower)alkyl which may have suitable substituent(s),
  $R^3$ is a leaving group,
  $R_a^4$ is lower alkyl,
  $R^7$ is hydrogen, ($C_1$–$C_5$)alkyl, aryl which may have suitable substituent(s), or ar($C_1$–$C_5$)alkyl which may have suitable substituent(s),
  $R_a^8$ is protected hydroxy,
  $Y^1$ is acid residue,
  $W^{1\ominus}$, $W^{2\ominus}$ and $W^{3\ominus}$ are each anion,
  $M^1$ is a heterocyclic group containing at least one nitrogen atom which has an imino protective group,
  $M^2$ is a heterocyclic group containing at least one nitrogen atom and

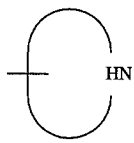

is a saturated heterocyclic group containing at least one nitrogen atom.

The starting compounds can be prepared by the following Processes.

Process (A)

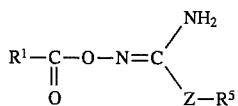

(IX)
or a salt thereof

↓ cyclization

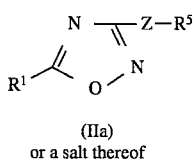

(IIa)
or a salt thereof

Process (B)

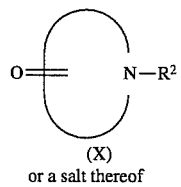

(X)
or a salt thereof

① ↓ 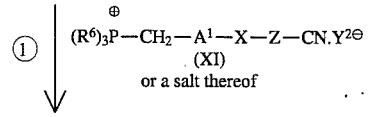

(XI)
or a salt thereof

-continued
Process (B)
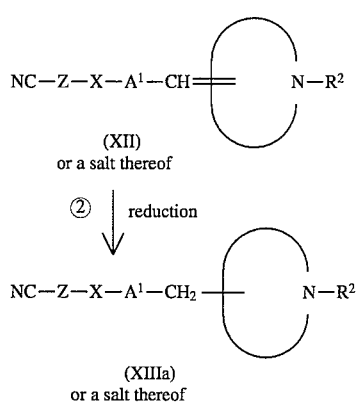
Process (E)
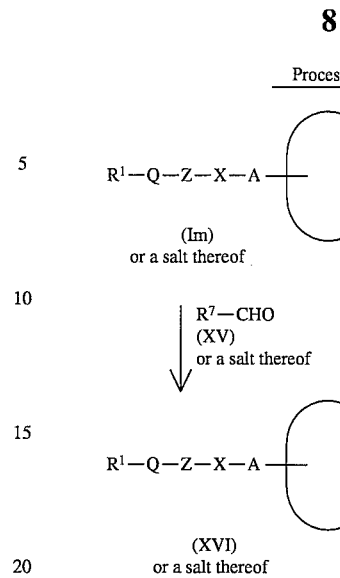
Process (C)
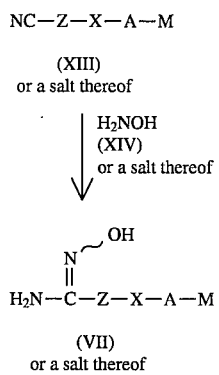
Process (F)
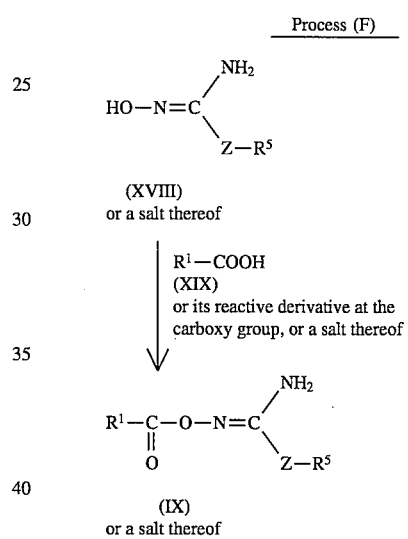
Process (D)
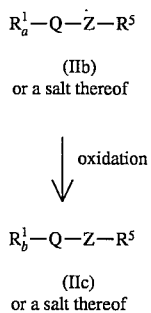
Process (G)
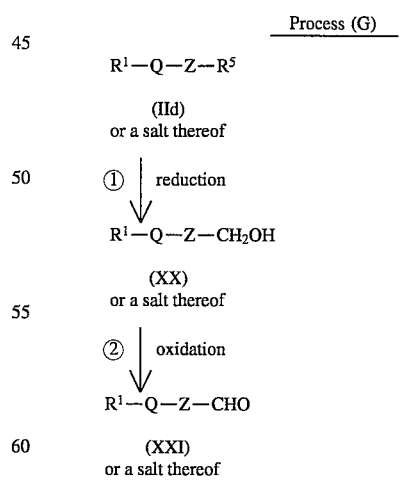

Process (H)

$R^1—Q—CHO$ (XXIa)
or a salt thereof $$CH_2\begin{matrix}COOH\\COOH\end{matrix}$$

(XXII)
or a salt thereof

↓

$R^1—Q—CH=CH—COOH$ (XXIII)
or a salt thereof

Process (I)

$R^1—Q—Z—COOH$ (II)
or its reactive derivative
at the carboxy group,
or a salt thereof $H_2N—CH_2—C≡CH$
(XXIV)
or its reactive derivative at the
amino group, or a salt thereof

↓

$R^1—Q—Z—CONH—CH_2—C≡CH$ (XXVa)
or a salt thereof

Process (J)

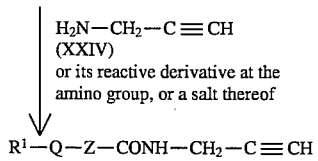

(In)
or a salt thereof $R^2—W_a^2$
(XXVI)
or a salt thereof

↓

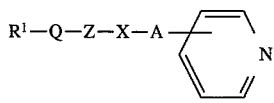

(XVIIa)
or a salt thereof

Process (K)

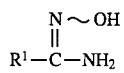

(XXVII)
or a salt thereof $$Y^3—\underset{\underset{O}{\|}}{C}—Z—R^5$$
(XXVIII)
or a salt thereof

↓

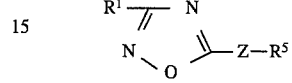

(IIe)
or a salt thereof

Process (L)

$Y^4—A—M$ (XXIX)
or a salt thereof

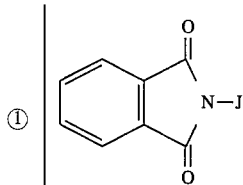

(XXX)

↓

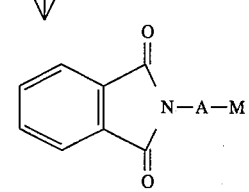

(XXXI)

② | $H_2NNH_2$
(XXXII)
or a salt thereof

↓

$H_2N—A—M$ (XXXIIIa)
or a salt thereof

Process (M)

$R^{10}—A—M^2$ (XXXIIIb)
or a salt thereof i) $R^7—CHO$
(XXXIV)
or a salt thereof
ii) reduction

↓

-continued

Process (M)

$R^{10}-A-M^3$ (XXXIIIc)
or a salt thereof

Process (N)

$R^{10}-A-M^2$ (XXXIIIb)

or a salt thereof

↓ acylation $R^{10}-A-M^4$ (XXXIIId)
or a salt thereof

Process (O)

$R^{10}-A-M^4$ (XXXIIId)
or a salt thereof

↓ reduction $R^{10}-A-M^5$ (XXXIIIe)
or a salt thereof

Process (P)

$OHC-M$ (XXXV)
or a salt thereof

↓ $(R^9O)_2\overset{O}{\overset{\|}{P}}CH_2CN$
(XXXVI)

$NC-CH=CH-M$ (XXXVII)
or a salt thereof

Process (Q)-①

$NC-CH=CH-M$ (XXXVII)
or a salt thereof

↓ reduction $NC-CH_2-CH_2-M$ (XXXVIIIa)
or a salt thereof

Process (Q)-②

$NC-A^1-M$ (XXXVIII)
or a salt thereof

↓ reduction $H_2N-CH_2-A^1-M$ (XXXIX)
or a salt thereof

Process (R)

$R^{11}-A^1-M$ (XXXX)
or a salt thereof

① ↓ $HCONH_2$
   (XXXXI)
   or a salt thereof $H_2NCO-A^1-M$ (XXXXII)
or a salt thereof ② ↓ reduction $H_2NCH_2-A^1-M$ (XXXIX)
or a salt thereof

Process (S)

$H_2N-\overset{S}{\overset{\|}{C}}-Z-X-A-M$ (XXXXIII)
or a salt thereof

① ↓ $H_2N-OH$
   (XIV)
   or a salt thereof $H_2N-\overset{N\sim OH}{\overset{\|}{C}}-Z-X-A-M$ (VII)
or a salt thereof ② ↓ $R^1-COOH$
   (XIX)
   or its reactive derivative
   at the carboxy group,
   or a salt thereof $H_2N-\overset{N\sim O\overset{O}{\overset{\|}{C}}-R^1}{\overset{\|}{C}}-Z-X-A-M$ (XXXXIV)
or a salt thereof Process (T)

(XXXXV)
or a salt thereof

↓ cyclization

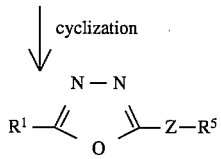

(IIf)
or a salt thereof wherein
$R^1$, $R^2$, $R^7$, X, Z, A, M, $M^2$, Q, $W^{1\ominus}$ and

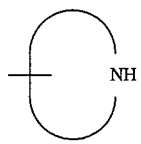

are each as defined above, $R_a^1$ is aryl having lower alkylthio, $R_b^1$ is aryl having lower alkylsulfinyl, or aryl having lower alkylsulfonyl, $R^5$ is carboxy or protected carboxy, $R^6$ is aryl, $R^9$ is lower alkyl, $R^{10}$ is hydroxy, protected hydroxy, amino or protected amino, $R^{11}$ is protected carboxy, $A^1$ is bond or $C_1$–$C_5$ alkylene, $Y^2$ is acid residue, $Y^3$ and $W_a^2$ are each a leaving group, $Y^4$ is hydroxy or a leaving group, J is an alkali metal, $M^3$ is a heterocyclic group containing at least one nitrogen atom which has a substituent selected from the group consisting of lower alkyl and ar(lower)alkyl which may have suitable substituent(s), $M^4$ is a heterocyclic group containing at least one nitrogen atom which has a substituent selected from the group consisting of ($C_1$–$C_5$)alkanoyl, aroyl which may have suitable substituent(s) and ar($C_1$–$C_5$)alkanoyl which may have suitable substituent(s), $M^5$ is a heterocyclic group containing at least one nitrogen atom which has a substituent selected from the group consisting of lower alkyl and ar(lower)alkyl which may have suitable substituent(s).

Suitable pharmaceutically acceptable salts of the object compound (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); an inorganic acid addition salt (e.g. hydrochloride, hydrobromide, sulfate, phosphate, etc.); an organic carboxylic or sulfonic acid addition salt (e.g. formate, acetate, trifluoroacetate, meleate, tartrate, fumarate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "ar(lower) alkyl", "lower alkylthio", "lower alkylsulfinyl" and "lower alkylsulfonyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, preferably one having 1 to 4 carbon atom(s).

Suitable "lower alkylene" may be straight or branched one having 1 to 6 carbon atom(s), such as methylene, ethylene, trimethylene, propylene, tetramethylene, pentamethylene, hexamethylene, and the like, preferably one having 1 to 4 carbon atom(s).

Suitable "lower alkynylene" may include ethynylene, propynylene, 1-(or 2-)butynylene, 1-(or 2- or 3-)pentynylene, and the like.

Suitable "aryl" and "aryl moiety" in the terms "ar(lower)alkyl" "ar(lower)alkenyl", "ar($C_1$–$C_5$)alkyl" and "ar($C_1$–$C_5$)alkanoyl" may include phenyl, naphthyl and the like, in which more preferable example may be phenyl.

Suitable "heterocyclic group" may include saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.;

saturated heterobicyclic group of the formula:

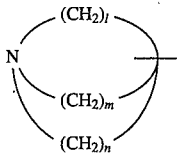

(wherein l, m and n are each integer of 1 to 6); and the like.

Suitable "substituent" in the term "heterocyclic group which may have suitable substituent(s)" may include lower alkyl (e.g., methyl, ethyl, propyl, isopropyl, butyl, isobutyl, t-butyl, pentyl, neopentyl, t-pentyl, hexyl, etc.), lower alkoxy (e.g., methoxy, ethoxy, propoxy, isopropoxy, isobutoxy, t-butoxy, pentyloxy, neopentyloxy, t-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono (or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine, iodine), carboxy, protected carboxy, hydroxy, protected hydroxy, aryl (e.g., phenyl, naphthyl, etc., ar(lower)alkyl such as phenyl(lower)alkyl (e.g., benzyl, phenethyl, phenylpropyl, etc.), carboxy(lower)alkyl, protected carboxy(lower)alkyl, nitro, amino, protected amino, di(lower)alkylamino (e.g., dimethylamino, diethylaminol, diisopropylamino, ethylmethylamino, isopropylmethylamino, ethylmethylamino, ethylpropylamino, etc.), hydroxy(lower)alkyl, protected hydroxy(lower)alkyl, acyl, cyano, mercapto, lower alkylthio (e.g., methylthio, ethylthio, propylthio, isopropylthio, butylthio, etc.), imino, and the like.

Suitable "heterocyclic group containing at least one nitrogen atom" may include unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, pyridyl and its N-oxide, dihydropyridyl, tetrahydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.; and the like.

Suitable "saturated heterocyclic group" in the term "saturated heterocyclic group containing at least one nitrogen atom" may include saturated 3 to 8-membered heteromonocyclic group containing 1 to 4 nitrogen atom(s) (e.g., azetidinyl, pyrrolidinyl, imidazolidinyl, piperidyl, pyrazolidinyl, piperazinyl, etc.) and the like.

Suitable "alkali metal" may include potassium, sodium and the like.

Suitable "leaving group" may include lower alkoxy (e.g. methoxy, ethoxy, propoxy, isopropoxy, butoxy, isobutoxy, t-butoxy, pentoxy, etc.), aryloxy (e.g. phenoxy, napthoxy, etc.), an acid residue or the like.

Suitable "acid residue" may be halogen (e.g. chlorine, bromine, iodines. etc.), sulfonyloxy (e.g. methanesulfonyloxy, benzenesulfonyloxy, toluenesulfonyloxy, etc.) or the like.

Suitable "substituent" in the terms "aryl which may have suitable substituent(s)", "ar(lower)alkyl which may have suitable substituent(s)", "ar(lower)alkenyl which may have suitable substituent(s)" and "ar($C_1$–$C_5$)alkyl which may have suitable substituent(s)" "aroyl which may have suitable substituent(s)" and "ar($C_1$–$C_5$)alkanoyl which may have suitable substituent(s)" may include lower alkyl (e.g., methyl, ethyl, propyl, isopropyl, butyl, isobutyl, tert-butyl, pentyl, neopentyl, tert-pentyl, hexyl, etc.), lower alkoxy (e.g., methoxy, ethoxy, propoxy, isopropoxy, isobutoxy, tert-butoxy, pentyloxy, neopentyloxy, tert-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g. fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine and iodine), carboxy, protected carboxy, hydroxy, protected hydroxy, aryl (e.g., phenyl, naphthyl, etc.), ar(lower)alkyl such as phenyl(lower)alkyl (e.g., benzyl, phenethyl, phenylpropyl, etc.), carboxy(lower)alkyl wherein lower alkyl moiety can be referred to the ones as exemplified above, protected carboxy(lower)alkyl wherein lower alkyl moiety can be referred to the ones as exemplified above and protected carboxy moiety can be referred to the ones as exemplified below, nitro, amino, protected amino, di(lower)alkylamino (e.g., dimethylamino, diethylamino, diisopropylamino, ethylmethylamino, isopropylmethylamino, ethylisopropylamino, etc.), hydroxy(lower)alkyl, protected hydroxy(lower)alkyl, acyl, cyano, mercapto, lower alkylthio (e.g., methylthio, ethylthio, propylthio, isopropylthio, butylthio, etc.), lower alkylsulfinyl (e.g., methylsulfinyl, ethylsulfinyl, propylsulfinyl, isopropylsulfinyl, butylsulfinyl, etc.), imino, and the like.

Suitable "$(C_1-C_5)$alkyl" and "$(C_1-C_5)$alkyl moiety" in the term "ar($C_1-C_5$)alkyl" may include straight or branched one having 1 to 5 carbon atom(s), such as methyl, ethyl, propyl, isopropyl, butyl, isobutyl, sec-butyl, tert-butyl, pentyl, tert-pentyl, and the like.

Suitable "protected hydroxy" may include acyloxy and the like.

Suitable "protected amino" may include acylamino and the like.

Suitable "an imino protective group" may include acyl and the like.

Suitable "acyl" and "acyl moiety" in the terms "acyloxy" and "acylamino" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:
Carbamoyl;
Aliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);
lower or higher alkoxycarbonyl (e.g. methoxycarbonyl ethoxycarbonyl, t-butoxycarbonyl, t-pentyloxycarbonyl, heptyloxycarbonyl, etc.);
lower or higher alkylsulfonyl (e.g. methylsulfonyl, ethylsulfonyl, etc.);
lower or higher alkoxysulfonyl (e.g. methoxysulfonyl, ethoxysulfonyl, etc.); or the like;
Aromatic acyl such as
aroyl (e.g. benzoyl, toluoyl, naphthoyl, etc.);
ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];
ar(lower)alkenoyl [e.g. phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.), etc.];
ar(lower)alkoxycarbonyl [e.g. phenyl(lower)alkoxycarbonyl (e.g. benzyloxycarbonyl, etc.), etc.]; aryloxycarbonyl (e.g. phenoxycarbonyl, naphthyloxycarbonyl, etc.); aryloxy(lower)alkanoyl (e.g. phenoxyacetyl, phenoxypropionyl, etc.); arylcarbamoyl (e.g. phenylcarbamoyl, etc.); arylthiocarbamoyl (e.g. phenylthiocarbamoyl, etc.); arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as heterocycliccarbonyl; heterocyclic(lower)alkanoyl (e.g. heterocyclicacetyl, heterocyclicpropanoyl, heterocyclicbutanoyl, heterocyclicpentanoyl, heterocyclichexanoyl, etc.);
heterocyclic(lower)alkenoyl (e.g. heterocyclicpropenoyl, heterocyclicbutenoyl, heterocyclicpentenoyl, heterocyclichexenoyl, etc.); heterocyclicglyoxyloyl; or the like; in which suitable heterocyclic moiety in the terms "heterocycliccarbonyl", "heterocyclic(lower)alkanoyl", heterocyclic(lower)alkenoyl and "heterocyclicglyoxyloyl" can be referred to the ones as mentioned above.

Suitable "lower alkenyl moiety" in the term "ar(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)-methyl-1-(or 2- or 3-)butenyl, and the like, in which more preferable example may be $C_2-C_4$ alkenyl.

Suitable "oxadiazolediyl" may include 1,2,4-oxadiazolediyl, 1,2,5-oxadiazolediyl and 1,3,4-oxadiazolediyl.

Suitable "$C_1-C_5$ alkylene" may be straight or branched one having 1 to 5 carbon atom(s), such as methylene, ethylene, trimethylene, propylene, tetramethylene, pentamethylene, and the like.

Suitable "protected carboxy" may include esterified carboxy and the like. An suitable examples of said ester moiety may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);
lower alkenyl ester (e.g., vinyl ester, allyl ester, etc.); lower alkynyl ester (e.g., ethynyl ester, propynyl ester, etc.);
lower alkoxyalkyl ester (e.g., methoxymethyl ester, ethoxymethyl ester, isopropoxymethyl ester, 1-methoxyethyl ester 1-ethoxyethyl ester, etc.);
lower alkylthioalkyl ester (e.g., methylthiomethyl ester, ethylthiomethyl ester, ethylthioethyl ester, isopropylthiomethyl ester, etc.);
mono(or di or tri)halo(lower)alkyl ester (e.g. 2-iodoethyl ester, 2,2,2-trichloroethyl ester, etc.);
lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);
lower alkanesulfonyl(lower)alkyl ester (e.g. mesylmethyl ester, 2-mesylethyl ester, etc.);
ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);
aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.);
tri(lower)alkyl silyl ester;
lower alkylthioester (e.g. methylthioester, ethylthioester, etc.) and the like.

Suitable "aroyl" may include benzoyl, naphthoyl and the like.

Suitable "$C_1-C_5$ alkanoyl" and "$C_1-C_5$ alkanoyl moiety" in the term "ar($C_1-C_5$)alkanoyl" may include formyl, acetyl, propanoyl, butanoyl, 2-methylpropanoyl, pentanoyl, 2,2-dimethylpropanoyl and the like.

The processes for preparing the object and starting compounds are explained in detail in the following.

Process (1)

The compound (Ia) or a salt thereof can be prepared by reacting the compound (III) or its reactive derivative at the amino group, or a salt thereof with the compound (II) or its reactive derivative at the carboxy group, or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound (III) with phosphorus trichloride or phosgene, and the like.

Suitable reactive derivative at the carboxy group of the compound (II) may include an acid halide, an acid anhydride, an activated amide, an activated ester, and the like. Suitable examples of the reactive derivatives may be an acid chloride; an acid azide;
a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. ethyl ester, cyanomethyl ester, methoxymethyl ester, dimethyliminomethyl $[(CH_3)_2N^+=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In case that the compounds (II) and (III) are in liquid, they can be used as a solvent.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to heating.
Process (2)

The compound (Ib) or a salt thereof can be prepared by reacting the compound (IV) or its reactive derivative at the amino group, or a salt thereof with the compound (V) or its reactive derivative at the carboxy group, or a salt thereof.

Suitable reactive derivative at the amino group of the compound (IV) may include Schiff's base type imino or its tautomeric enamine type isomer formed by the reaction of the compound (IV) with a carbonyl compound such as aldehyde, ketone or the like; a silyl derivative formed by the reaction of the compound (IV) with a silyl compound such as bis(trimethylsilyl)acetamide, mono(trimethylsilyl)acetamide [e.g. N-(trimethylsilyl)acetamide], bis(trimethylsilyl)urea or the like;
a derivative formed by reaction of the compound (IV) with phosphorus trichloride or phosgene, and the like.

Suitable reactive derivative at the carboxy group of the compound (V) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl $[(CH_3)_2N^+=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (V) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in mixture with water.

In case that the compounds (IV) and (V) are in liquid, they can be used as a solvent.

In this reaction, when the compound (V) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxasolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, alkali metal hydride, tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process (3)

The compound (Ic) or a salt thereof can be prepared by reacting the compound (VI) or a salt thereof with the compound (VII) or a salt thereof.

The reaction is usually carried out in a conventional solvent such as chloroform, ether, tetrahydrofuran, benzene, N,N-dimethylformamide, N,N-dimethylacetamide or any other organic solvent which does not adversely influence the reaction.

The reaction temperature is not critical and the reaction is usually carried out under cooling to heating.

The reaction is usually carried out in the presence of an inorganic or an organic base such as an alkali metal hydroxide, an alkali metal hydrogencarbonate, alkali metal carbonate, alkali metal hydride (e.g. sodium hydride, etc.), alkali metal acetate, tri(lower)alkylamine, pyridine base (e.g. pyridine, lutidine, picoline, dimethylaminopyridine, etc.), N-(lower)alkylmorpholine, N,N-di(lower)alkylbenzylamine, N,N-di(lower)alkylaniline or the like. When the base and/or the starting compound are in liquid, they can be used also as a solvent.

The reaction is preferably carried out in the presence of a dehydrating agent [e.g. Molecular Sieves (trademark: Linde Corporation), etc.].

Process (4)

The compound (Id) or a salt thereof can be prepared by reacting the compound (Ia) or a salt thereof with the compound (VIII).

The reaction is usually carried out in a conventional solvent such as chloroform, ether, tetrahydrofuran, benzene, N,N-dimethylformamide, N,N-dimethylacetamide or any other organic solvent which does not adversely influence the reaction.

The reaction temperature is not critical and the reaction is usually carried out under cooling to warming.

The reaction is usually carried out in the presence of an inorganic or an organic base such as an alkali metal hydroxide, an alkali metal hydrogencarbonate, alkali metal carbonate, alkali metal hydride (e.g. sodium hydride, etc.), tri(lower)alkylamine, pyridine base (e.g. pyridine dimethylaminopyridine, etc.) or the like.

When the base and/or the starting compound are in liquid, they can be used also as a solvent.

Process (5)

The compound (Ie) or a salt thereof can be prepared by subjecting the compound (XVI) or a salt thereof to reduction reaction.

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.) and the like.

The reduction is usually carried out in a conventional solvent which does not adversely influence the reaction such as water, alcohol (e.g., methanol, ethanol, propanol, etc.), tetrahydrofuran, dioxane, N,N-dimethylformamide, or a mixture thereof.

Additionally, in case that the above-mentioned acids to be used in chemical reduction are in liquid, they can also be used as a solvent.

The reaction temperature is not critical and the reaction is usually carried out under cooling to warming.

Process (6)

The compound (Ig) or a salt thereof can be prepared by subjecting the compound (If) or a salt thereof to elimination reaction of the imino protective group.

Suitable method of this elimination reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]-non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

Among these solvents, hydrophilic solvents may be used in a mixture with water.

The reaction temperature is not critical and the reaction is usually carried out under cooling to warming.

(ii) For reduction:

Reduction is carried out in a conventional manner, including chemical reduction and catalytic reduction.

Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.) and the like.

The reduction is usually carried out in a conventional solvent which does not adversely influence the reaction such as water, alcohol (e.g., methanol, ethanol, propanol, etc.), N,N-dimethylformamide, or a mixture thereof.

Additionally, in case that the above-mentioned acids to be used in chemical reduction are in liquid, they can also be used as a solvent.

The reaction temperature is not critical and the reaction is usually carried out under cooling to warming.

Process (7)

The compound (Ih) or a salt thereof can be prepared by subjecting the compound (XVII) or a salt thereof to reduction reaction.

This reaction can be carried out in a similar manner to that of the aforementioned Process (5), and therefore the reagents to be used and the reaction conditions (e.g., solvent, reaction temperature, etc.) can be referred to those of the Process (5).

Process (8)

The compound (Ij) or a salt thereof can be prepared by subjecting the compound (Ii) or a salt thereof to elimination reaction of the hydroxy protective group.

This reaction can be carried out in a similar manner to that of the aforementioned Process (6), and therefore the reagents to be used and the reaction conditions (e.g., solvent, reaction temperature, etc.) can be referred to those of the Process (6).

Process (9)

The compound (Ik) or a salt thereof can be prepared by subjecting the compound (Ij) or a salt thereof to oxidation reaction.

Oxidation is carried out in a conventional manner, and suitable oxidizing agent may be a combination of dimethyl sulfoxide and N,N'-dicyclohexylcarbodiimide, lower alkanoic anhydride (e.g., acetic anhydride, etc.), phosphorus pentoxide, sulfurtrioxide-pyridine, N-halosuccinimide (e.g., N-chlorosuccinimide, etc.), oxalyl chloride or the like.

The reaction may be carried out in the presence of an acid.

Suitable acid may include an organic acid [e.g. formic acid, acetic acid, propionic acid, trichloroacetic acid, trifluoroacetic acid, etc.,] and an inorganic acid [e.g. hydrochloric acid, hydrobromic acid, phosphoric acid, sulfuric acid, hydrogen chloride, hydrogen bromide, etc.] and the like.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g. sodium methoxide, sodium ethoxide, etc.), pyridine (e.g. pyridine, lutidine, picoline, dimethylaminopyridine, etc.), N-(lower)alkylmorpholine, N,N-di(lower)alkylbenzylamine, N,N-di(lower)alkylaniline or the like.

When the base, the acid and/or the starting compound are in liquid, they can be also as a solvent.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to warming.

Process (10)

The compound (II) or a salt thereof can be prepared by reacting the compound (XXV) or a salt thereof with the compound (XXXXVI) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

When the starting compound is in liquid, it can be also used as a solvent.

The reaction is preferably carried out in the presence of the catalyst [e.g., copper halide (e.g., copper (I) chloride, etc.) etc.].

The reaction temperature is not critical and the reaction is usually carried out under cooling to warming.

Process (A)

The compound (IIa) or a salt thereof can be prepared by subjecting the compound (IX) or a salt thereof to cyclization.

This reaction can be carried out in accordance with the method disclosed in the Preparation 2 described later or a similar manner thereto.

Process (B)-①

The compound (XII) or a salt thereof can be prepared by reacting the compound (X) or a salt thereof with the compound (XI) or a salt thereof.

This reaction can be carried out in accordance with the method disclosed in the Preparation 3 described later or a similar manner thereto.

Process (B)-②

The compound (XIIIa) or a salt thereof can be prepared by subjecting the compound (XII) or a salt thereof to reduction reaction.

This reaction can be carried out in accordance with the method disclosed in the Preparation 4 described later or a similar manner thereto.

Process (C)

The compound (VII) or a salt thereof can be prepared by reacting the compound (XIII) or a salt thereof with the compound (XIV) or a salt thereof.

This reaction can be carried out in accordance with the method disclosed in the Preparation 5 described later or a similar manner thereto.

Process (D)

The compound (IIc) or a salt thereof can be prepared by subjecting the compound (IIb) or a salt thereof to oxidation reaction.

Oxidation is carried out in a conventional manner, which is capable of oxidizing a sulfur atom to an oxidized sulfur atom, and suitable oxidizing reagent may be oxygen acid such as periodate (e.g. sodium periodate, potassium periodate, etc.), peroxy acid such as peroxybenzoic acids (e.g. peroxybenzoic acid, m-chloroperoxybenzoic acid, etc.), and the like.

The reaction is usually carried out in a conventional solvent such as water, alcohol (e.g., methanol, ethanol, isopropyl alcohol, etc.), tetrahydrofuran, dioxane, dichloromethane, chloroform, N,N-dimethylacetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to warming.

Process (E)

The compound (XVI) or a salt thereof can be prepared by reacting the compound (Im) or a salt thereof with the compound (XV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be also used as a solvent.

The reaction is preferably carried out in the presence of a dehydrating agent [e.g. Molecular Sieves, etc.].

Suitable "anion" may include anion derived from the materials used in this reaction such as acid residue [e.g., halogen (e.g. fluorine, chlorine, bromine, iodine), etc.], OH$^-$ and the like.

Process (F)

The compound (IX) or a salt thereof can be prepared by reacting the compound (XVIII) or a salt thereof with the compound (XIX) or its reactive derivative at the carboxy group, or a salt thereof.

Suitable reactive derivative at the carboxy group of the compound (XIX) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. ethyl ester, cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (XIX) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In case that the compounds (XVIII) and (XIX) are in liquid, they can be used as a solvent.

In this reaction, when the compound (XIX) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process (G)-①

The compound (XX) or a salt thereof can be prepared by subjecting the compound (IId) or a salt thereof to reduction reaction.

This reaction can be carried out in a similar manner to that of the aforementioned Process (5), and therefore the reagents to be used and the reaction conditions (e.g., solvent, reaction temperature, etc.) can be referred to those of the Process (5).
Process (G)-

The compound (XXI) or a salt thereof can be prepared by subjecting the compound (XX) or a salt thereof to oxidation reaction.

This reaction can be carried out in a similar manner to that of the aforementioned Process (9), and therefore the reagents to be used and the reaction conditions (e.g., solvent, reaction temperature, etc.) can be referred to those of the Process (9).
Process (H)

The compound (XXIII) or a salt thereof can be prepared by reacting the compound (XXIa) or a salt thereof with the compound (XXII) or a salt thereof.

This reaction can be carried out in the manner disclosed in Preparation 11-(1) or similar manners thereto.
Process (I)

The compound (XXVa) or a salt thereof can be prepared by reacting the compound (II) or its reactive derivative at the carboxy group, or a salt thereof with the compound (XXIV) or its reactive derivative at the amino group, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).
Process (J)

The compound (XVIIa) or a salt thereof can be prepared by reacting the compound (In) or a salt thereof with the compound (XXVI) or a salt thereof.

This reaction can be carried out in the manner disclosed in Preparation 13-(1) or similar manners thereto.
Process (K)

The compound (IIe) or a salt thereof can be prepared by reacting the compound (XXVII) or a salt thereof with the compound (XXVIII) or a salt thereof.

This reaction can be carried out in the manner disclosed in Preparation 14 or similar manners thereto.
Process (L)-

The compound (XXXI) can be prepared by reacting the compound (XXIX) or a salt thereof with the compound (XXX) or a salt thereof.

This reaction can be carried out in the manner disclosed in Preparations 17-(1) and 20 or similar manners thereto.
Process (L)-②

The compound (XXXIIIa) or a salt thereof can be prepared by reacting the compound (XXXI) with the compound (XXXII) or a salt thereof.

This reaction can be carried out in the manner disclosed in Preparation 18-(1) and 21 or similar manners thereto.
Process (M)

The compound (XXXIIIc) or a salt thereof can be presented by reacting the compound (XXXIIIb) or a salt thereof with the compound (XXXIV) or a salt thereof and then by subjecting the resultant compound to reduction reaction.

This reaction can be carried out in the manner disclosed in Preparation 19-(1) or similar manners thereto.
Process (N)

The compound (XXXIIId) or a salt thereof can be prepared by subjecting the compound (XXXIIIb) or a salt thereof to acylation reaction.

Suitable acylating agent to be used in the present acylation reaction may include the compound of the formula:

$$R_a^2\text{—OH} \qquad \text{(XXXXVII)}$$

(wherein $R_a^2$ is $C_1$–$C_5$ alkanoyl aroyl which may have suitable substituent(s), or ar($C_1$–$C_5$) alkanoyl which may have suitable substituent(s).)
or its reactive derivative or a salt thereof.

Suitable reactive derivative of the compound (XXXXVII) may include an acid halide, an acid anhydride, an activated amide, an activated ester, isocyanate, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridine, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them according to the kind of the compound (XXXXVII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XXXXVII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphoenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like. The reaction temperature is not critical, and the reaction is usually carried out under cooling to heating.

Process (O)

The compound (XXXIIIe) or a salt thereof can be prepared by subjecting the compound (XXXIIId) or a salt thereof to reduction reaction.

This reaction can be carried out in a similar manner to that of the aforementioned Process (5), and therefore the reagents to be used and the reaction conditions (e.g., solvent, reaction temperature, etc.) can be referred to those of the Process (5).

Process (P)

The compound (XXXVII) or a salt thereof can be prepared by reacting the compound (XXXV) or a salt thereof with the compound (XXXVI).

This reaction can be carried out in the manner disclosed in Preparation 24 or similar manners thereto.

Process (Q)-①

The compound (XXXVIIIa) or a salt thereof can be prepared by subjecting the compound (XXXVII) or a salt thereof to reduction reaction.

This reaction can be carried out in the manner disclosed in Preparation 25 or similar manners thereto.

Process (Q)-②

The compound (XXXIX) or a salt thereof can be prepared by subjecting the compound (XXXVIII) or a salt thereof to reduction reaction.

This reaction can be carried out in the manner disclosed in Preparation 26 or similar manners thereto.

Process (R)-①

The compound (XXXXII) or a salt thereof can be prepared by reacting the compound (XXXX) or a salt thereof with the compound (XXXXI) or a salt thereof.

This reaction can be carried out in the manner disclosed in Preparation 27 or similar manners thereto.

Process (R)-②

The compound (XXXIX) or a salt thereof can be prepared by subjecting the compound (XXXXII) or a salt thereof to reduction reaction.

This reaction can be carried out in a similar manner to that of the aforementioned Process (5), and therefore the reagents to be used and the reaction conditions (e.g., solvent, reaction temperature, etc.) can be referred to those of the Process (5).

Process (S)-①

The compound (VII) or a salt thereof can be prepared by reacting the compound (XXXXIII) or a salt thereof with the compound (XIV) or a salt thereof.

This reaction can be carried out in the manner disclosed in Preparation 29 or similar manners thereto.

Process (S)-②

The compound (XXXXIV) or a salt thereof can be prepared by reacting the compound (VII) or a salt thereof with the compound (XIX) or its reactive derivative at the carboxy group, or a salt thereof.

This reaction can be carried out in a similar manner to that of the aforementioned Process (F), and therefore the reagents to be used and the reaction conditions (e.g., solvent, reaction temperature, etc.) can be referred to those of the Process (F).

Process (T)

The compound (IIf) or a salt thereof can be prepared by subjecting the compound (XXXXV) or a salt thereof to cyclization reaction.

This reaction can be carried out in the manner disclosed in Preparation 31-(1) or similar manners thereto.

Suitable salts of the object and starting compounds and their reactive derivatives in Processes (1)~(10) and (A)~(T) can be referred to the ones as exemplified for the compound (I).

Preferred embodiments of the object compound (I) are as follows.

$R^1$ is lower alkyl, a heterocyclic group which may have 1 to 3 suitable substituent(s) [more preferably unsaturated 5 or 6-membered heteromonocyclic group containing 1 to 4 nitrogen atom(s), unsaturated 5 or 6-membered heteromonocyclic group containing 1 to 2 sulfur atom(s) or saturated heterobicyclic group of the formula:

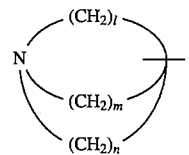

(wherein l, m and n are each integer of 1 to 6 (more preferably 1 to 3)), each of which may have 1 to 2 substituent(s) selected from the group consisting of lower alkyl, lower alkenyl, lower alkynyl, lower alkoxy, lower alkylthio, lower alkylsulfinyl, cyano, nitro, mono(or di or tri)halo(lower)alkyl and acyl; most preferably pyridyl, thienyl or quinuclidinyl, each of which may have cyano], aryl which may have 1 to 3 substituent(s) selected from the group consisting of lower alkyl, lower alkoxy, nitro, halogen, mono(or di or tri)halo(lower)alkyl, lower alkylthio, lower alkylsulfinyl, cyano and acyl [more preferably phenyl which may have 1 to 2 substituent(s) selected from the group consisting of lower alkyl, lower alkoxy, nitro, halogen, mono(or di or tri)halo(lower)alkyl, lower alkylthio, lower alkylsulfinyl, cyano, lower alkylsulfonyl and lower alkanoyl;

most preferably phenyl which may have a substituent selected from the group consisting of lower alkyl, lower alkoxy, nitro, halogen, mono(or di or tri)halo(lower)alkyl, lower alkylthio, lower alkylsulfinyl, cyano, lower alkylsulfonyl and lower alkanoyl], ar(lower)alkyl which may have 1 to 3 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl [more preferably phenyl(lower)alkyl which may have 1 to 2 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl; most preferably phenyl(lower)alkyl which may have nitro], or ar(lower)alkenyl which may have 1 to 3 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl [more preferably phenyl(lower)alkenyl which may have 1 to 2 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl; most preferably phenyl(lower)alkenyl which may have cyano or nitro], is oxadiazolediyl (more preferably

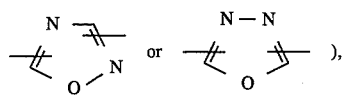

), is bond or vinyl, is bond, a group of the formula:

(in which $R^4$ is hydrogen or lower alkyl), a group of the formula:

(in which $R^8$ is hydroxy or protected hydroxy [more preferably acyloxy, most preferably lower alkanoyloxy]),

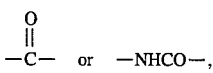

A is bond, lower alkylene or lower alkynylene,
M is unsaturated 5 or 6-membered heteromonocyclic group containing 1 to 4-nitrogen atom(s) or saturated 5 or 6-membered heteromonocyclic group containing 1to 4 nitrogen atom(s), each of which may have one substituent selected from the group consisting of lower alkyl, an imino protective group and ar(lower)alkyl which may have 1 to 3 suitable substituent(s) [more preferably piperidyl, piperazinyl, pyrrolidinyl, tetrahydropyridyl or pyridyl, each of which may have one substituent selected from the group consisting of lower alkyl, acyl and phenyl(lower)alkyl which may have 1 to 2 substituent(s) selected from the group consisting of halogen, cyano, nitro, lower alkyl, lower alkoxy and lower alkylthio;
most preferably piperidyl, piperazinyl, pyrrolidinyl, tetrahydropyridyl or pyridyl, each of which may have one substituent selected from the group consisting of lower alkyl, lower alkoxycarbonyl and
phenyl(lower)alkyl which may have a substituent selected from the group consisting of halogen, cyano, nitro, lower alkyl and lower alkoxy].

The object compound (I) of this invention and pharmaceutically acceptable salts thereof possess strong inhibitory activity against acetylcholinesterase, but hardly possess inhibitory activity against butyrylcholinesterase. That is, the object compound (I) of this invention and pharmaceutically acceptable salts thereof are selective inhibitors of acetylcholinesterase and muscarinic agonist and therefore useful for the treatment of disorders in the central nervous system such as amnesia, dementia [e.g., senile dementia of Alzheimer type, vascular dementia, etc.], cerebrovascular disease or the like.

In order to illustrate the usefulness of the object compound (I), the pharmacological test data of the compound (I) are shown in the following.

[1] Test Compound
(a) 5-(Quinuclidin-3-yl)-3-[{2-(1-benzylpiperidin-4-yl)ethyl}carbamoyl]-1,2,4-oxadiazole dihydrochloride
(b) 3-[{2-(1-Benzylpiperidin-4-yl)ethyl}carbamoyl]-5-(4-nitrophenyl)-1,2,4-oxadiazole fumarate

[2] Inhibition of acetylcholinesterase
(i) Test Method:
The ability to inhibit acetylcholinesterase was determined by the method (enzyme assay) described in Clinica Chimica Acta, 115 (1981) 163–170. The acetylcholinesterase used in this test was obtained from rat's corpus striatum.

[3] Test Result:

| Test compound | $IC_{50}$ (M) |
|---|---|
| (a) | $8.0 \times 10^{-9}$ |
| (b) | $1.7 \times 10^{-9}$ |

The object compound (I) or its pharmaceutically acceptable salts can usually be administered to mammals including human being in the form of a conventional pharmaceutical composition such as capsule, micro-capsule, tablet, granule, powder, troche, syrup, aerosol, inhalation, solution, injection, suspension, emulsion, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 10 mg/kg, 1 to 4 times a day. However, the above dosage may be increased or decreased according to age, weight, conditions of the patient or the administering method.

The following Examples and Preparations are given for the purpose of illustrating the present invention in more detail.

PREPARATION 1

(1) To a solution of 4-nitrobenzoyl chloride (10 g) in tetrahydrofuran (150 ml) was added a suspension of ethyl 2-amino-2-hydroxyiminoacetate (7.1 g) in tetrahydrofuran (30 ml). After stirring for 2 hours, the precipitates were collected by filtration and washed with diethyl ether to afford ethyl 2-amino-2-(4-nitrobenzoyloxyimino)acetate (12.19 g).
mp: 192°–194° C.
IR (Nujol): 3425, 3325, 1740, 1710 cm$^{-1}$
NMR (DMSO-d$_6$, δ): 1.31 (3H, t, J=7 Hz), 4.32 (2H, q, J=7 Hz), 7.3–7.5 (2H, br s), 8.33 (2H, d, J=9 Hz), 8.45 (2H, d, J=9 Hz)

The following compounds were obtained according to a similar manner to that of Preparation 1-(1).
(2) Ethyl 2-amino-2-(4-methoxybenzoyloxyimino)acetate
mp: 171°–172° C.
IR (Nujol): 3475, 3360, 1725, 1080 cm$^{-1}$
NMR (DMSO-d$_6$, δ): 1.31 (3H, t, J=7.1 Hz), 3.86 (3H, s), 4.30 (2H, q, J=7.1 Hz), 7.04 (2H, d, J=9 Hz), 7.14 (2H, br s), 8.16 (2H, d, J=9 Hz)
(3) Ethyl 2-amino-2-nicotinoyloxyiminoacetate
mp: 178°–179° C.
IR (Nujol): 3420, 3260, 1730, 1640, 1590 cm$^{-1}$
NMR (DMSO-d$_6$, δ): 1.31 (3H, t, J=7.1Hz), 4.32 (2H, q, J=7.1Hz), 7.31 (2H, s), 7.59 (1H, ddd, J=0.8, 4.9, 8.0Hz), 8.55 (1H, ddd, J=2.0, 2.0, 8.0 Hz), 8.84 (1H, dd, J=2.0, 4.9 Hz), 9.34 (1H, dd, J=0.8, 2.0 Hz)

Mass (m/z): 237 (M$^+$)

(4) Ethyl 2-amino-2-(4-trifluoromethylbenzoyloxyimino)acetate mp: 205°–206° C.

IR (Nujol): 3420, 3330, 1740, 1720, 1630, 1600 cm$^{-1}$

NMR (DMSO-d$_6$, δ): 1.31 (3H, t, J=7.1 Hz), 4.32 (2H, q, J=7.1 Hz), 7.32 (2H, br), 7.90 (2H, d, J=8.3 Hz), 8.41 (2H, d, J=8.3 Hz)

Mass (m/z): 304 (M$^+$)

PREPARATION 2

(1) A suspension of ethyl 2-amino-2-(4-nitrobenzoyloxyimino)acetate (2.8 g) and powdered molecular sieves 3A (5 g) was refluxed for 24 hours. After evaporating the solvent, the residue was subjected to column chromatography on silica gel (200 ml) with methylene chloride-n-hexane as eluent. The fractions containing the object compound were combined and evaporated in vacuo to afford 3-ethoxycarbonyl-5-(4-nitrophenyl)-1,2,4-oxadiazole (1.8 g).

mp: 75°–77° C.

IR (Nujol): 1750, 1605, 1210 cm$^{-1}$

NMR (CDCl$_3$, δ): 1.49 (3H, t, J=7.1 Hz), 4.57 (2H, q, J=7.1Hz), 8.44 (4H, s)

The following compounds were obtained according to a similar manner to that of Preparation 2-(1).

(2) 3-Ethoxycarbonyl-5-(4-methoxyphenyl)-1,2,4-oxadiazole mp: 75°–77° C.

IR (Nujol): 1750, 1605, 1210 cm$^{-1}$

NMR (CDCl$_3$, δ): 1.47 (3H, t, J=7.1 Hz), 3.90 (3H, s), 4.54 (2H, q, J=7.1 Hz), 7.03 (2H, d, J=9 Hz), 8.16 (2H, d, J=9 Hz)

(3) 3-Ethoxycarbonyl-5-(3-nitrophenyl)-1,2,4-oxadiazole mp: 75°–77° C.

IR (Nujol): 1730, 1620, 900, 720 cm$^{-1}$

NMR (CDCl$_3$, δ): 1.50 (3H, t, J=7.1 Hz), 4.58 (2H, q, J=7.1 Hz), 7.8–7.9 (1H, m), 8.5–8.6 (2H, m), 7.07–9.07 (1H, m)

(4) 3-Ethoxycarbonyl-5-(4-methylthiophenyl)-1,2,4-oxadiazole mp: 82°–83° C.

IR (Nujol): 1745, 1595, 1200, 740 cm$^{-1}$

NMR (CDCl$_3$, δ): 1.47 (3H, t, J=7.1 Hz), 2.55 (3H, s), 4.55 (2H, q, J=7.1 Hz), 7.35 (2H, d, J=8.6 Hz), 8.09 (2H, d, J=8.6 Hz)

Mass (m/z): 264 (M$^+$)

(5) 3-Ethoxycarbonyl-5-(pyridin-3-yl)-1,2,4-oxadiazole mp: 45°–46° C.

IR (Nujol): 1740, 1600, 1580 cm$^{-1}$

NMR (CDCl$_3$, δ): 1.49 (3H, t, J=7.1 Hz), 4.57 (2H, q, J=7.1 Hz), 7.55 (1H, ddd, J=0.6, 4.9, 7.9 Hz), 8.50 (1H, ddd, J=1.6, 1.6, 8.0 Hz), 8.88 (1H, dd, J=1.6, 4.9Hz), 9.45 (1H, dd, J=0.8, 1.6 Hz)

Mass (m/z): 219 (M$^+$)

(6) 3-Ethoxycarbonyl-5-(4-trifluoromethylphenyl)-1,2,4-oxadiazole mp: 104°–105° C.

IR (Nujol): 3330, 3100, 1750, 1640, 1590 cm$^{-1}$

NMR (DMSO-d$_6$, δ): 1.38 (3H, t, J=7.1 Hz), 4.47 (2H, q, J=7.1 Hz), 7.89 (2H, d, J=8.3 Hz), 8.37 (2H, d, J=8.3 Hz)

Mass (m/z): 286 (M$^+$)

PREPARATION 3

To a suspension of 4-cyanobutyltriphenylphosphonium bromide (21.80 g) in tetrahydrofuran (100 ml) was added potassium tert-butoxide (5.76 g) in tetrahydrofuran (50 ml) over 30 minutes at 0° C. After 1 hour, a solution of 1-benzyl-4-piperidone (8.84 g) was added to the mixture over 30 minutes at 0° C. The mixture was stirred at ambient temperature for 1 hour, poured into ice-water and extracted with ethyl acetate. The extract was washed with brine, dried over magnesium sulfate and evaporated in vacuo. The residue was chromatographed on alumina eluting with chloroform/hexane (1:1) and the fractions containing the object compound were combined and evaporated to afford 1-benzyl-4-(4-cyanobutylidene)piperidine (9.8 g) as an oil.

IR (Film): 2250, 1600, 1495 cm$^{-1}$

NMR (CDCl$_3$, δ): 1.65–1.76 (2H, m), 2.10–2.48 (12H, m), 3.51 (2H, s), 5.05 (1H, t, J=7.2 Hz), 7.21–7.36 (5H, m)

Mass (m/z): 254 (M$^+$)

PREPARATION 4

A mixture of 1-benzyl-4-(4-cyanobutylidene)piperidine (8.8 g) and platinum dioxide (1.2 g) in tetrahydrofuran (150 ml) was hydrogenated at atmospheric pressure for 12 hours. After the catalyst was filtered out, the filtrate was evaporated in vacuo. The residue was chromatographed on silica gel eluting with chloroform/methanol (95:5) and the fractions containing the object compound were combined and evaporated to afford 1-benzyl-4-(4-cyanobutyl)piperidine (5.0 g) as an oil.

IR (Film): 2250, 1600, 1490 cm$^{-1}$

NMR (CDCl$_3$, δ): 1.23–1.27 (5H, m), 1.41–1.45 (2H, m), 1.52–1.71 (4H, m), 1.86–1.96 (2H, m), 2.33 (2H, t, J=6.8 Hz), 2.84–2.90 (2H, m), 3.48 (2H, s), 7.21–7.32 (5H, m)

Mass (m/z): 255 (M$^+$)

PREPARATION 5

A mixture of 1-benzyl-4-(4-cyanobutyl)piperidine (2.20 g), potassium carbonate (3.56 g) and hydroxylamine hydrochloride (2.39 g) was heated under reflux for 20 hours. After cooling, the mixture was filtered and evaporated in vacuo. The residue was dissolved in ether, filtered and recrystalized to afford 5-(1-benzylpiperidin-4-yl)-1-hydroxyiminopentylamine (1.56 g).

mp: 82°–85° C. IR (Nujol): 3500, 3480, 3150, 1670, 1640, 1595 cm$^{-1}$ NMR (CDCl$_3$, δ): 1.08–1.15 (7H, m), 1.45–1.64 (4H, m), 1.90 (2H, t, J=10.0 Hz), 2.11 (2H, t, J=7.9 Hz), 2.85 (2H, d, J=10.8 Hz), 3.48 (2H, s), 4.52 (2H, s), 7.21–7.31 (5H, s) Mass (m/z): 273 (M$^+$)

PREPARATION 6

The following compounds were obtained according to a similar manner to that of Preparation 1-(1).

(1) Ethyl 2-amino-2-(2-nitrobenzoyloxyimino)acetate mp: 176°–177° C. NMR (DMSO-d$_6$, δ): 1.29 (3H, t, J=7.1 Hz), 4.28 (2H, q, J=7.1 Hz), 7.16–7.20 (2H, br), 7.78–8.00 (3H, m), 8.09–8.17 (1H, m) Mass (m/z): 282 (M$^+$+1)

(2) Ethyl 2-amino-2-(4-chlorobenzoyloxyimino)acetate

NMR (DMSO-d$_6$, δ): 1.31 (3H, t, J=7.1 Hz), 4.31 (2H, q, J=7.1 Hz), 7.24–7.28 (2H, br), 7.60 (2H, d, J=8.6 Hz), 8.22 (2H, d, J=8.6 Hz)

(3) Ethyl 2-amino-2-(4-pyridylcarbonyloxyimino)acetate mp: 163°–165° C. IR (Nujol): 3420, 3320, 1740, 1620 cm$^{-1}$ NMR (CDCl$_3$, δ): 1.31 (3H, t, J=7.1 Hz), 4.32 (2H, q, J=7.1 Hz), 7.30–7.35 (2H, br), 8.10 (2H, d, J=6.1 Hz), 8.80 (2H, d, J=6.1 Hz)

(4) Ethyl 2-amino-2-acetoxyiminoacetate mp: 161°–162° C. IR (Nujol): 3410, 3300, 1750, 1620 cm$^{-1}$ NMR (DMSO-d$_6$, δ): 1.27 (3H, t, J=7.1 Hz), 2.11 (3H, s), 4.26 (2H, q, J=7.1 Hz), 6.97–7.01 (2H, br) Mass (m/z): 174 (M$^+$)

(5) 5-(1-Benzylpiperidin-4-yl)-1-(4-nitrobenzoyloxyimino)pentylamine mp: 110°–112° C. IR (Film): 3500, 3330, 1730, 1640, 1600 cm$^{-1}$ NMR (CDCl$_3$, δ): 1.25–1.35 (7H, m), 1.57–1.68 (4H, m), 1.92–2.03 (2H, m), 2.31–2.38 (2H, m), 2.89–2.95 (2H, m), 4.84–4.88 (2H, br), 7.27–7.34 (5H, m), 8.20 (2H, d, J=9.0 Hz), 8.29 (2H, d, J=9.0 Hz)

Elemental Analysis Calcd. for C$_{24}$H$_{30}$N$_4$O$_4$: C 65.73, H 6.89, N 12.77 Found: C 65.58, H 7.05, N 12.65

PREPARATION 7

The following compounds were obtained according to a similar manner to that of Preparation 2-(1).

(1) 3-Ethoxycarbonyl-5-(4-cyanophenyl)-1,2,4-oxadiazole mp: 127°–129° C. IR (Nujol): 2220, 1740 cm$^{-1}$ (2) 3-Ethoxycarbonyl-5-(2-nitrophenyl)-1,2,4-oxadiazole mp: 176°–178° C. IR (Nujol): 1750 cm$^{-1}$ NMR (DMSO-d$_6$, δ): 1.37 (3H, t, J=7.1 Hz), 4.47 (2H, q, J=7.1 Hz), 7.98–8.07 (2H, m), 8.11–8.18 (1H, m), 8.26–8.35 (1H, m) Mass (m/z): 263 (M$^+$)

(3) 3-Ethoxycarbonyl-5-(4-chlorophenyl)-1,2,4-oxadiazole mp: 92°–94° C. IR (Nujol): 1740, 1600 cm$^{-1}$ NMR (DMSO-d$_6$, δ): 1.40 (3H, t, J=7.1 Hz), 4.45 (2H, q, J=7.1 Hz), 7.73 (2H, d, J=8.6 Hz), 8.16 (2H, d, J=8.6 Hz) Mass (m/z): 252 (M$^+$)

(4) 3-Ethoxycarbonyl-5-(4-pyridyl)-1,2,4-oxadiazole mp: 65°–67° C. IR (Nujol): 3500, 3400, 1730 cm$^{-1}$ NMR (DMSO-d$_6$, δ): 1.39 (3H, t, J=7.1 Hz), 4.47 (2H, q, J=7.1 Hz), 8.08 (2H, d, J=6.1 Hz), 8.91 (2H, d, J=6.1 Hz)

(5) 3-Ethoxycarbonyl-5-(4-fluorophenyl)-1,2,4-oxadiazole mp: 64°–65° C. IR (Nujol): 1740, 1600 cm$^{-1}$ NMR (CDCl$_3$, δ): 1.48 (3H, t, J=7.1 Hz), 4.55 (2H, J=7.1 Hz), 7.20–7.31 (2H, m), 8.20–8.30 (2H, m) Mass (m/z): 236 (M$^+$)

(6) 3-Ethoxycarbonyl-5-methyl-1,2,4-oxadiazole mp: 31°–32° C. IR (Nujol): 1740 cm$^{-1}$ NMR (CDCl$_3$, δ): 1.45 (3H, t, J=7.2 Hz), 2.70 (3H, s), 4.51 (2H, q, J=7.2 Hz)

(7) 3-Ethoxycarbonyl-5-(2-cyanothiophen-5-yl)-1,2,4-oxadiazole mp: 118°–120° C. IR (Nujol): 2220, 1740, 1600 cm$^{-1}$ NMR (CDCl$_3$, δ): 1.48 (3H, t, J=7.1 Hz), 4.55 (2H, q, J=7.1 Hz), 7.72 (1H, d, J=4.1 Hz), 7.99 (1H, d, J=4.1 Hz)

(8) 3-Ethoxycarbonyl-5-{(E)-2-(4-nitrophenyl)vinyl}-1,2,4-oxadiazole mp: 187°–188° C. IR (Nujol): 1735, 1640, 1210, 840 cm$^{-1}$ NMR (DMSO-d$_6$, δ): 1.35 (3H, t, J=7.1 Hz), 4.43 (2H, q, J=7.1 Hz), 7.71 (2H, d, J=16.5 Hz), 8.13 (2H, d, J=16.5 Hz), 8.13 (2H, d, J=8.8 Hz), 8.30 (2H, d, J=8.8 Hz)

(9) 3-Ethoxycarbonyl-5-(4-acetylphenyl)-1,2,4-oxadiazole mp: 100°–101° C. IR (Nujol): 1740, 1680, 1220 cm$^{-1}$ NMR (DMSO-d$_6$, δ): 1.37 (3H, t, J=7.1 Hz), 2.67 (3H, s), 4.46 (2H, q, J=7.1 Hz), 8.18 (2H, d, J=8.4 Hz), 8.30 (2H, d, J=8.4 Hz)

(10) 3-Ethoxycarbonyl-5-{(E)-2-(4-cyanophenyl)vinyl}-1,2,4-oxadiazole mp: 159°–160° C. IR (Nujol): 2225, 1735, 1630, 1220 cm$^{-1}$ NMR (DMSO-d$_6$, δ): 1.35 (3H, t, J=7.1 Hz), 4.43 (2H, q, J=7.1 Hz), 7.67 (2H, d, J=16.5 Hz), 7.95 (2H, d, J=8.4 Hz), 8.06 (2H, d, J=16.5 Hz), 8.07 (2H, d, J=8.4 Hz),

(11) 3-Ethoxycarbonyl-5-(4-nitrobenzyl)-1,2,4-oxadiazole mp: 120°–121° C. IR (Nujol): 1740, 1350, 725 cm$^{-1}$ NMR (DMSO-d$_6$, δ): 1.31 (3H, t, J=7.1 Hz), 4.39 (2H, q, J=7.1 Hz), 4.68 (2H, s), 7.68 (2H, d, J=9.3 Hz), 8.25 (2H, d, J=9.3 Hz)

PREPARATION 8

(1) To a mixture of 4-fluorobenzoic acid (2.0 g), ethyl 2-amino-2-hydroxyiminoacetate (2.07 g) and 4-dimethylaminopyridine (0.52 g) in methylene chloride (30 ml) was added 1-ethyl-3-(3-dimethylaminopropyl)carbodiimide (2.87 ml) at 0° C. under stirring. After stirring at ambient temperature for 1 hour, diethyl ether (10 ml) was added thereto and the resulting precipitate was filtered off, washed with diethyl ether, and dried in vacuo to give ethyl 2-amino-2-(4-fluorobenzoyloxyimino)acetate (3.2 g).

mp: 196°–198° C. IR (Nujol): 3400, 3300, 1740, 1620 cm$^{-1}$ NMR (DMSO-d$_6$, δ): 1.31 (3H, t, J=7.1 Hz), 4.31 (2H, q, J=7.1 Hz), 7.23–7.25 (2H, br), 7.31–7.41 (2H, m), 8.25–8.33 (2H, m) Mass (m/z): 254 (M$^+$)

The following compound was obtained according to a similar manner to that of Preparation 8-(1).

(2) Ethyl 2-amino-2-[(2-cyanothiophen-5-yl)carbonyloxyimino]acetate mp: 196°–197° C. IR (Nujol): 3420, 3320, 2220, 1730, 1620 cm$^{-1}$ NMR (DMSO-d$_6$, δ): 1.30 (3H, t, J=7.1 Hz), 4.31 (2H, q, J=7.1 Hz), 7.34–7.40 (2H, br), 8.10 (1H, d, J=4.0 Hz), 8.32 (1H, d, J=4.0 Hz) Mass (m/z): 267 (M$^+$)

PREPARATION 9

(1) To a solution of 5-(4-cyanophenyl)-3-ethoxycarbonyl-1,2,4-oxadiazole (5.0 g) in methanol (50 ml)—tetrahydrofuran (50 ml) was added sodium borohydride (0.93 g) at 0° C. After stirring at 5°–10° C. for 1 hour, the mixture was poured into water and extracted with ethyl acetate. The extract was washed with water and brine, dried over magnesium sulfate, and evaporated in vacuo. The residue was recrystallized from diethyl ether to give 5-(4-cyanophenyl)-3-hydroxymethyl-1,2,4-oxadiazole (4.0 g).

mp: 138°–140° C. IR (Nujol): 3330, 2220 cm$^{-1}$ NMR (DMSO-d$_6$, δ): 4.65 (2H, d, J=6.1 Hz), 5.84 (1H, t, J=6.1 Hz), 8.11 (2H, d, J=8.2 Hz), 8.29 (2H, d, J=8.2 Hz)

The following compound was obtained according to a similar manner to that of Preparation 9-(1).

(2) 3-Hydroxymethyl-5-(4-nitrophenyl)-1,2,4-oxadiazole mp: 155°–156° C. IR (Nujol): 3350, 1600 cm$^{-1}$ NMR (DMSO-d$_6$, δ): 4.68 (2H, d, J=6.0 Hz), 5.85 (1H, t, J=6.0 Hz), 8.35 (2H, d, J=9.1 Hz), 8.44 (2H, d, J=9.1 Hz) Mass (m/z): 220 (M$^+$ of free compound-1)

PREPARATION 10

(1) A mixture of 5-(4-cyanophenyl)-3-hydroxymethyl-1,2,4-oxadiazole (4.08 g), N,N'-dicyclohexylcarbodiimide (20.92 g) and o-phosphoric acid (9.94 g) in dimethyl sulfoxide (80 ml) was stirred at ambient temperature. After 1 hour, the mixture was poured into water and extracted with ethyl acetate. The extract was washed with water and brine, dried over magnesium sulfate, and evaporated in vacuo. The residue was recrystallized from ether to give 5-(4-cyanophenyl)-3-formyl-1,2,4-oxadiazole (2.17 g).

mp: 168°–170° C. (dec.) IR (Nujol): 3320, 2230, 1715 cm$^{-1}$ NMR (DMSO-d$_6$, δ): 8.11 (2H, d, J=8.5 Hz), 8.28 (2H, d, J=8.5 Hz)

The following compound was obtained according to a similar manner to that of Preparation 10-(1).

(2) 3-Formyl-5-(4-nitrophenyl)-1,2,4-oxadiazole mp: 169°–171° C. (dec.) IR (Nujol): 1710 cm$^{-1}$ NMR (DMSO-d$_6$, δ): 8.37 (2H, d, J=9.1 Hz), 8.45 (2H, d, J=9.1 Hz)

PREPARATION 11

(1) A mixture of 5-(4-cyanophenyl)-3-formyl-1,2,4-oxadiazole (2.0 g), malonic acid (4.18 g) and piperidine (0.50 ml) in pyridine (20 ml) was refluxed for 1 hour. After cooling to room temperature, the mixture was evaporated in vacuo. The residue was dissolved in ethyl acetate, acidified to pH 2.0 with 4N hydrochloric acid washed with water and brine, dried over magnesium sulfate, and evaporated in vacuo. The residue was recrystallized from ethanol to give 3-{(E)-2-carboxyvinyl}-5-(4-cyanophenyl)-1,2,4-oxadiazole (1.2 g).

mp: 222°–225° C. (dec.) IR (Nujol): 2230, 1690 cm$^{-1}$ NMR (DMSO-d$_6$, δ): 6.92 (1H, d, J=15.8 Hz), 7.51 (1H, d, J=15.8 Hz), 8.13 (2H, d, J=8.6 Hz), 8.30 (2H, d, J=8.6 Hz)

The following compound was obtained according to a similar manner to that of Preparation 11-(1).

(2) 3-{(E)-2-Carboxyvinyl}-5-(4-nitrophenyl)-1,2,4-oxadiazole mp: 206°–208° C. (dec.) IR (Nujol): 1690 cm$^{-1}$ NMR (DMSO-d$_6$, δ): 6.93 (1H, d, J=15.8 Hz), 7.53 (1H, d, J=15.8 Hz), 8.38–8.49 (4H, m)

PREPARATION 12

The following compound was obtained according to a similar manner to that of Example 1.

3-{(2-Propynyl)carbamoyl}-5-(4-nitrophenyl)-1,2,4-oxadiazole mp: 188°–189° C. (dec.) IR (Nujol): 3330, 3250, 1680 cm$^{-1}$ NMR (DMSO-d$_6$, δ): 3.20 (1H, t, J=2.5 Hz), 4.08 (2H, d, J=2.5 Hz), 8.40 (2H, d, J=9.1 Hz), 8.49 (2H, d, J=9.1 Hz), 9.60–9.64 (1H, br) Mass (m/z): 272 (M$^+$)

Elemental Analysis Calcd. for C$_{12}$H$_8$N$_4$O$_4$: C 52.94, H 2.96, N 20.58 Found: C 52.85, H 2.76, N 20.29

PREPARATION 13

(1) A mixture of 3-[{2-(pyridin-4-yl)ethyl}carbamoyl]-5-(4-cyanophenyl)-1,2,4-oxadiazole (0.72 g) and 4-fluorobenzyl iodide (0.80 g) in dimethyl sulfoxide (5 ml) was stirred at 50° C. for 1 hour. After cooling to room temperature, the mixture was evaporated in vacuo. The residue was recrystallized from diethyl ether to give 3-[[2-{1-(4-fluorobenzyl)-4-pyridinio}ethyl]carbamoyl]-5-(4-cyanophenyl)-1,2,4-oxadiazole iodide (1.0 g).

mp: 202°–204° C. IR (Nujol): 3200, 2230, 1680 cm$^{-1}$ NMR (DMSO-d$_6$, δ): 3.21–3.24 (2H, m), 3.70–3.73 (2H, m), 5.79 (2H, s), 7.29 (2H, dd, J=8.8, 8.8 Hz), 7.60 (2H, dd, J=5.4, 8.8 Hz), 8.10 (2H, d, J=6.7 Hz), 8.15 (2H, d, J=8.6 Hz), 8.30 (2H, d, J=8.6 Hz), 9.09 (2H, d, J=6.7 Hz), 9.26–9.30 (1H, m) Mass (m/z): 428 (M$^+$-I$^\ominus$)

The following compounds were obtained according to a similar manner to that of Preparation 13-(1).

(2) 3-[{2-[1-Benzyl-4-pyridinio)ethyl}carbamoyl]-5-(4-cyanophenyl)-1,2,4-oxadiazole iodide mp: 208°–209° C. IR (Nujol): 3180, 2230, 1680, 1635 cm$^{-1}$ NMR (DMSO-d$_6$, δ): 3.18–3.25 (2H, m), 3.68–3.74 (2H, m), 5.82 (2H, s), 7.41–7.51 (5H, m), 8.10 (2H, d, J=6.6 Hz), 8.15 (2H, d, J=8.5 Hz), 8.30 (2H, d, J=8.5 Hz), 9.11 (2H, d, J=6.6 Hz), 9.25–9.31 (1H, m)

Elemental Analysis Calcd. for C$_{24}$H$_{20}$IN$_5$O$_2$: C 53.64, H 3.75, N 13.03 Found: C 53.57, H 3.67, N 12.95

(3) 3-[{2-(1-Benzyl-4-pyridinio)ethyl}carbamoyl]-5-(4-nitrophenyl)-1,2,4-oxadiazole iodide mp: 207°–208° C. IR (Nujol): 3200, 1680, 1630 cm$^{-1}$ NMR (DMSO-d$_6$, δ): 3.20–3.25 (2H, m), 3.70–3.75 (2H, m), 5.81 (2H, s), 7.41–7.48 (5H, m), 8.10 (2H, d, J=6.5 Hz), 8.39 (2H, d, J=9.0 Hz), 8.49 (2H, d, J=9.0 Hz), 9.10 (2H, d, J=6.5 Hz), 9.30–9.34 (1H, m) Mass (m/z): 430 (M$^+$-I$^\ominus$)

(4) 3-[[2-{1-(4-Fluorobenzyl)-4-pyridinio}ethyl]-carbamoyl]-5-(4-nitrophenyl)-1,2,4-oxadiazole iodide mp: 198°–200° C. IR (Nujol): 3500, 3410, 3300, 1680, 1630, 1600 cm$^{-1}$ NMR (DMSO-d$_6$, δ): 3.23 (2H, t, J=6.5 Hz), 3.71–3.75 (2H, m), 5.82.(2H, s), 7.30 (2H, dd, J=8.8, 8.8 Hz), 7.62 (2H, dd, J=5.4, 8.8 Hz), 8.12 (2H, d, J=6.5 Hz), 8.38 (2H, d, J=9.0 Hz), 8.49 (2H, d, J=9.0 Hz), 9.12 (2H, d, J=6.5 Hz), 9.30–9.35 (1H, m) Mass (m/z): 448 (M$^+$-I$^\ominus$)

Elemental Analysis Calcd. for C$_{23}$H$_{19}$FIN$_5$O$_4$: C 47.28, H 3.28, N 11.98 Found: C 47.30, H 3.33, N 11.85

PREPARATION 14

A mixture of 4-nitrobenzamide oxime (4 g) and ethyl chlorooxoacetate (3.01 g) in dioxane (200 ml) was refluxed for 1 hour, and then borontrifluoride (1 ml) was added thereto. The whole mixture was refluxed for 12 hours. After being cooled to room temperature, the solvent was evaporated in vacuo. The residue was diluted with ethyl acetate (100 ml), washed with a saturated potassium carbonate aqueous solution, dried over magnesium sulfate and evaporated in vacuo. The residue was purified by column chromatography on silica gel with a mixture of dichloromethane and hexane (1:1) as eluent. The fractions containing the object product were collected and evaporated in vacuo to afford 5-ethoxycarbonyl-3-(4-nitrophenyl)-1,2,4-oxadiazole.

mp: 117°–118° C. IR (Nujol): 1740, 1345, 720 cm$^{-1}$ NMR (DMSO-d$_6$, δ): 1.39 (3H, t, J=7.1 Hz), 4.49 (2H, q, J=7.1 Hz), 8.32 (2H, d, J=10.9 Hz), 8.43 (2H, d, J=10.9 Hz)

PREPARATION 15

A solution of di-tert-butyl-dicarbonate (1.70 g) in methylene chloride (5 ml) was added dropwise to a mixture of 4-(2-hydroxyethyl)piperidine (1.0 g) and triethylamine (1.08 ml) in methylene chloride (10 ml) at 5° C. After stirring at ambient temperature for 1 hour, the reaction mixture was poured into water. The organic layer was washed with water and brine, dried over magnesium sulfate, and evaporated in vacuo. The residue was chromatographed on silica eluting with 3% methanol in chloroform and the fractions containing the object product were collected and evaporated to give 1-tert-butoxycarbonyl-4-(2-hydroxyethyl)piperidine (1.80 g) as an oil.

IR (Film): 3400, 1670 cm$^{-1}$ NMR (CDCl$_3$, δ): 1.09–1.13 (2H, m), 1.45 (9H, s), 1.50–1.71 (5H, m), 2.62–2.75 (2H, m), 3.67–3.74 (2H, m), 4.04–4.11 (2H, m) Mass (m/z): 229 (M⁺)

PREPARATION 16

(1) A solution of methanesulfonyl chloride (0.51 ml) in methylene chloride (5 ml) was added dropwise to a mixture of 4-(2-hydroxyethyl)-1-tert-butoxycarbonylpiperidine (1.43 g) and triethylamine (0.91 ml) at 5° C. After stirring at ambient temperature for 1 hour, the mixture was poured into ice water and extracted with ethyl acetate. The extract was washed with water and brine, dried over magnesium sulfate and evaporated in vacuo to give 1-tert-butoxycarbonyl-4-(2-mesyloxyethyl)piperidine (1.37 g).

mp: 83°–84° C. IR (Nujol): 1665 cm⁻¹ NMR (CDCl₃, δ): 1.04–1.24 (2H, m), 1.45 (9H, m), 1.56–1.76 (5H, m), 2.63–2.76 (2H, m), 3.02 (3H, m), 4.07–4.13 (2H, m), 4.26–4.32 (2H, m) Mass (m/z): 307 (M⁺)

The following compound was obtained according to a similar manner to that of Preparation 16-(1).

(2) 1-(3-Methoxybenzoyl)-4-(2-mesyloxyethyl)piperidine

IR (Film): 3450, 2940, 1620, 1580 cm⁻¹ NMR (CDCl₃, δ): 1.20–1.24 (2H, br), 1.71–1.76 (5H, m), 2.66–2.70 (2H, br), 2.90–3.01 (2H, br), 3.06 (3H, s), 3.86 (3H, s), 4.26–4.32 (2H, s), 6.92 (1H, s), 6.93–6.99 (2H, m), 7.25–7.33 (1H, m) Mass (m/z): 340 (M⁺–1)

PREPARATION 17

(1) A mixture of 1-tert-butoxycarbonyl-4-(2-mesyloxyethyl)piperidine (1.20 g) and potassium phthalimide (0.80 g) in N,N-dimethylformamide (15 ml) was stirred at 40° C. for 2 hours. The mixture was poured into water and extracted with ethyl acetate. The extract was washed with water, and dried over magnesium sulfate and evaporated in vacuo to give N-[2-[1-tert-butoxycarbonylpiperidin-4-yl]ethyl]phthalimide (1.12 g).

mp: 112°–114° C. IR (Nujol): 1770, 1710, 1670 cm⁻¹ NMR (DMSO-d₆, δ): 0.91–1.07 (2H, m), 1.39 (9H, s), 1.48–1.58 (3H, m), 1.67–1.73 (2H, m), 2.60–2.70 (2H, m), 3.57–3.64 (2H, m), 3.88–3.94 (2H, m), 7.80–7.90 (4H, m) Mass (m/z): 358 (M⁺)

The following compound was obtained according to a similar manner to that of Preparation 17-(1).

(2) N-[2-[1-(3-Methoxybenzoyl)piperidin-4-yl]ethyl]phthalimide IR (Film): 3460, 2930, 1770, 1710, 1620 cm⁻¹ NMR (DMSO-d₆, δ): 1.10–1.13 (2H, m), 1.54–1.75 (5H, m), 2.71–2.94 (2H, br), 3.59–3.65 (4H, m), 3.78 (3H, s), 6.89 (1H, s), 6.98–7.02 (2H, m), 7.31–7.39 (1H, m), 7.80–7.90 (4H, m) Mass (m/z): 391 (M⁺–1)

PREPARATION 18

(1) A mixture of N-[2-[1-tert-butoxycarbonylpiperidin-4-yl]ethyl]phthalimide (1.0 g) and hydrazine hydrate (0.16 ml) in ethanol (10 ml) was refluxed for 1 hour. After cooling to room temperature, the mixture was evaporated. The residue was chromatographed on alumina eluting with chloroform and the fractions containing the object product were collected and evaporated to give 2-[1-tert-butoxycarbonylpiperidin-4-yl]ethylamine (0.4 g) as an oil.

IR (Film): 3460, 1680 cm⁻¹ NMR (CDCl₃, δ): 1.00–1.18 (4H, m), 1.34–1.41 (3H, m), 1.45 (9H, s), 2.62–2.77 (4H, m), 4.04–4.10 (2H, br) Mass (m/z): 228 (M⁺)

The following compounds were obtained according to a similar manner to that of Preparation 18-(1).

(2) 2-[1-(3-Methoxybenzoyl)piperidin-4-yl]ethylamine

IR (Film): 3360, 3300, 2920, 1620 cm⁻¹ NMR (CDCl₃, δ): 1.17–1.21 (2H, m), 1.38–1.47 (4H, m), 1.56–1.67 (3H, m), 2.71–2.78 (2H, m), 2.80–2.96 (2H, m), 3.82 (3H, s), 6.92 (1H, s), 6.93–7.02 (2H, m), 7.26–7.34 (1H, m) Mass (m/z): 262 (M⁺)

(3) 2-(1-Benzylpiperazin-4-yl)ethylamine

IR (Film): 3350, 2940, 2800, 1590 cm⁻¹ NMR (CDCl₃, δ): 2.38–2.48 (10H, m), 2.75–2.81 (2H, m), 3.51 (2H, s), 7.19–7.41 (5H, m) Mass (m/z): 220 (M⁺+1)

PREPARATION 19

(1) A mixture of 4-(2-hydroxyethyl)piperidine (21.5 g), 4-fluorobenzaldehyde (17.5 ml) and p-toluene sulfonic acid (3 mg) in benzene (200 ml) was refluxed with separating water as the benzene azeotrope. After 2 hours, the mixture was evaporated in vacuo. The residue was dissolved in methanol (200 ml) and sodium borohydride (6.3 g) was added thereto at 5° C. After stirring at ambient temperature for 1 hour, the mixture was evaporated in vacuo. 4N Hydrochloric acid (200 ml) was added to the residue and washed with ethyl acetate. The aqueous layer was made basic to pH 10 with potassium carbonate and extracted with ethyl acetate. The extract was washed with water and brine, and dried over magnesium sulfate, and evaporated in vacuo to give 1-(4-fluorobenzyl)-4-(2-hydroxyethyl)piperidine (32.0 g) as an oil.

IR (Film): 3330, 1740 cm⁻¹ NMR (CDCl₃, δ): 1.21–1.58 (5H, m), 1.55–1.69 (2H, m), 1.87–2.24 (2H, m), 2.81–2.87 (2H, m), 3.43 (2H, s), 3.66 (2H, t, J=6.5 Hz), 6.92–7.08 (2H, m), 7.23–7.36 (2H, m)

The following compound was obtained according to a similar manner to that of Preparation 19-(1).

(2) 4-Ethoxycarbonyl-1-benzylpiperidine

IR (Film): 3400, 1730 cm⁻¹

PREPARATION 20

To a mixture of 1-(4-fluorobenzyl)-4-(2-hydroxyethyl)piperidine (10.0 g), triphenylphosphine (13.04 g) and phthalimide (6.65 g) in tetrahydrofuran (100 ml) was added dropwise a solution of diethyl diazenedicarboxylate (7.7 ml) in tetrahydrofuran (50 ml). After stirring overnight at ambient temperature, the mixture was evaporated in vacuo. The residue was dissolved in ethyl acetate and washed with water and brine, and dried over magnesium sulfate, and evaporated in vacuo. The residue was suspended with hexane—ether (100 ml—100 ml) and the precipitates were removed by filtration. The filtrate was evaporated in vacuo and the residue was recrystallized from hexane to give N-[2-[1-(4-fluorobenzyl)piperidin4-yl]ethyl]phthalimide (9.23 g).

mp: 53°–54° C. IR (Nujol): 1760, 1700, 1600 cm⁻¹ NMR (DMSO-d₆, δ): 1.11–1.90 (3H, m), 1.47–1.56 (2H, m), 1.66–1.71 (2H, m), 1.80–1.91 (2H, m), 2.71–2.77 (2H, m), 3.39 (2H, s), 3.56–3.63 (2H, m), 7.07–7.17 (2H, m), 7.27–7.34 (2H, m), 7.80–7.89 (4H, m)

PREPARATION 21

A mixture of N-[2-[1-(4-fluorobenzyl)piperidin-4-yl] ethyl]phthalimide (12.7 g) and hydrazine hydrate (2.02 ml) in ethanol (150 ml) was refluxed for 2 hours. After cooling to room temperature, the mixture was evaporated in vacuo. The residue was chromatographed on alumina eluting with chloroform and the fractions containing the object product were collected and evaporated to give 2-[1-(4-fluorobenzyl)piperidin-4-yl]ethylamine (4.5 g) as an oil.

IR (Film): 3350, 1600 cm$^{-1}$ NMR (CDCl$_3$, δ): 1.19–1.41 (7H, m), 1.61–1.66 (2H, m), 1.86–1.98 (2H, m), 2.67–2.74 (2H, m), 2.80–2.86 (2H, m), 3.43 (2H, s), 6.92–7.04 (2H, m), 7.21–7.30 (2H, m) Mass (m/z): 237 (M$^+$+1)

PREPARATION 22

To a mixture of 4-(2-hydroxyethyl)piperidine (5.0 g) and triethylamine (5.39 ml) in methylene chloride (50 ml) was added dropwise a solution of 3-methoxybenzoyl chloride (5.44 ml) in methylene chloride (15 ml) at 0° C. After stirring at ambient temperature for 1 hour, the mixture was poured into water and extracted with ethyl acetate. The extract was washed with water and brine, and dried over magnesium sulfate, and evaporated in vacuo. The residue was chromatographed on silica eluting with chloroform and the fractions containing the object product were collected and evaporated to give 2-[1-(3-methoxybenzoyl)piperidin-4-yl]ethanol (9.6 g) as an oil.

IR (Film): 3400, 1620, 1580 cm$^{-1}$ NMR (CDCl$_3$, δ): 1.15–1.20 (2H, br), 1.49–1.58 (2H, m), 1.70–1.90 (5H, m), 2.80–3.00 (2H, br), 3.66–3.84 (2H, m), 3.82 (3H, s), 4.67–4.75 (1H, br), 6.92 (1H, s), 6.93–6.96 (2H, m), 7.26–7.31 (1H, m) Mass (m/z): 262 (M$^+$−1)

PREPARATION 23

A solution of 2-[1-(3-methoxybenzoyl)piperidin-4-yl]ethylamine (4.5 g) in tetrahydrofuran (40 ml) was added dropwise to a suspension of lithium aluminum hydride (1.63 g) in tetrahydrofuran (50 ml) under refluxing. After 30 minutes, the mixture was cooled to 0° C., and ethyl acetate (5 ml), water (2 ml), 4N sodium hydroxide (4 ml), water (2 ml) and magnesium sulfate were added thereto successively. The resulting precipitates were removed out by filtration and the filtrate was evaporated in vacuo. The residue was chromagographed on alumina eluting with 2% methanol in chloroform to give 2-[1-(3-methoxybenzyl)piperidin-4-yl] ethylamine (1.8 g) as an oil.

NMR (CDCl$_3$, δ): 1.21–1.49 (7H, m), 1.61–1.66 (2H, m), 1.88–1.99 (2H, m), 2.59–2.75 (2H, m), 2.83–2.89 (2H, m), 3.46 (2H, s), 3.70 (3H, s), 6.76–6.81 (1H, m), 6.88–6.91 (2H, m), 7.18–7.27 (1H, m) Mass (m/z): 248 (M$^{30}$)

PREPARATION 24

A solution of 1-benzyl-4-formylpiperidine (4.5 g) in tetrahydrofuran (20 ml) was added dropwise to a suspension of diethyl cyanomethylphosphonate (4.31 g) and sodium hydride (0.97 g, 60% suspension in oil) in tetrahydrofuran (30 ml) at 0° C. under stirring. After stirring for 1 hour at ambient temperature, the mixture was poured into water and extracted with ethyl acetate. The extract was washed with water and brine and dried over magnesium sulfate, and evaporated in vacuo to give (E)-3-(1-benzylpiperidin-4-yl)-2-propenenitrile (5.5 g) as an oil.

NMR (DMSO-d$_6$, δ): 1.34–1.73 (5H, m), 1.93–2.16 (2H, m), 2.81–2.93 (2H, m), 3.50 (2H, s), 5.22–5.33 (1H, m), 6.27–6.73 (1H, m), 7.19–7.39 (5H, m) Mass (m/z): 226 (M$^+$)

PREPARATION 25

A mixture of (E)-3-(1-benzylpiperidin-4-yl)-2-propenenitrile (5.5 g) and platinum(IV) oxide (0.5 g) in methanol (70 ml) was hydrogenated at atmospheric pressure for 8 hours. After platinum(IV) oxide was removed by filtration, the filtrate was evaporated in vacuo to give 3-(1-benzylpiperidin-4-yl)propanenitrile (2.7 g) as an oil.

IR (Film): 2240 cm$^{-1}$ NMR (CDCl$_3$, δ): 1.16–1.48 (3H, m), 1.55–1.65 (4H, m), 1.70–2.02 (2H, m), 2.02–2.39 (2H, m), 2.86–2.91 (2H, m), 3.49 (2H, s), 7.23–7.41 (5H, m) Mass (m/z): 228 (M$^+$)

PREPARATION 26

A mixture of 3-(1-benzylpiperidin-4-yl)propanenitrile (0.5 g), Raney nickel (0.3 ml) and a conc. ammonia aqueous solution (1 ml) in ethanol (10 ml) was hydrogenated at atmospheric pressure for 6 hours. After Raney nickel was removed by filtration, the filtrate was evaporated in vacuo. The residue was chromatographed on alumina eluting with 2% methanol in chloroform and the fractions containing the object product were collected and evaporated to give 3-(1-benzylpiperidin-4-yl)propylamine (0.4 g) as an oil.

IR (Film): 3350, 3270 cm$^{-1}$ NMR (CDCl$_3$, δ): 1.23–1.44 (9H, m), 1.62–1.67 (2H, m), 1.86–1.97 (2H, m), 2.63–2.70 (2H, m), 2.84–2.90 (2H, m), 3.48 (2H, s), 7.23–7.32 (5H, m)

PREPARATION 27

To a mixture of 1-benzyl-4-ethoxycarbonylpiperidine (6.88 g) and formamide (3.71 ml) in N,N-dimethylformamide (30 ml) was added 28% sodium methoxide solution in methanol (4.0 ml) at 100° C. under stirring. After stirring at 100° C. for 1 hour, the mixture was evaporated in vacuo. The residue was dissolved in ethyl acetate and washed with water and brine and dried over magnesium sulfate, and evaporated in vacuo. The residue was recrystallized from ether to give 1-benzyl-4-carbamoylpiperidine (2.8 g).

mp: 158°–160° C. NMR (DMSO-d$_6$, δ): 1.44–1.70 (4H, m), 1.84–2.13 (3H, m), 2.77–2.83 (2H, m), 3.43 (2H, s), 7.23–7.40 (5H, m) Mass (m/z): 218 (M$^+$)

PREPARATION 28

A solution of 1-benzyl-4-carbamoylpiperidine (2.5 g) in tetrahydrofuran (10 ml) was added dropwise to 1N solution of diborane-tetrahydrofuran complex in tetrahydrofuran (34.3 ml) at 0° C. and then the mixture was refluxed for 3 hours. After cooling to room temperature, 6N hydrochloric acid (10 ml) was added thereto. The mixture was stirred overnight and concentrated in vacuo. The residue was dissolved in ethyl acetate and made basic with 5N sodium hydroxide. The separated organic layer was washed with water and brine and dried over magnesium sulfate, and evaporated in vacuo to give (1-benzylpiperidin-4-yl)methylamine (1.4 g) as an oil.

NMR (CDCl$_3$, δ): 1.22–1.31 (2H, m), 1.68–2.05 (5H, m), 2.35–2.45 (2H, m), 2.54–2.61 (2H, m), 2.87–2.92 (2H, m), 3.49 (2H, s), 7.26–7.37 (5H, m) Mass (m/z): 204 (M$^+$)

PREPARATION 29

To a solution of hydroxylamine hydrochloride (0.23 g) in hot ethanol (10 ml) was added 1N sodium ethoxide (3.44 ml) and stirred at ambient temperature for 20 minutes. The resulting precipitates were removed filtration. To the filtrate was added 2-acetoxy-5-(1-benzylpiperidin-4-yl)pentanethioamide (1.0 g) and the mixture was stirred overnight. The solution was evaporated in vacuo and the residue was extracted with ethyl acetate. The extract was washed with water, dried over magnesium sulfate and evaporated in vacuo to give 2-acetoxy-5-(1-benzylpiperidin-4-yl)-1-hydroxyiminopentylamine (0.68 g) as an oil.

IR (Film): 3500, 3400, 1730, 1670, 1580 cm$^{-1}$ NMR (CDCl$_3$, δ): 1.10–1.30 (7H, m), 1.60–1.64 (2H, m), 1.71–1.88 (2H, m), 1.93–1.99 (2H, m), 2.09 (3H, s), 2.86–2.92 (2H, m), 3.51 (2H, m), 4.63 (2H, s), 5.21 (1H, t, J=7.1 Hz), 7.24–7.33 (5H, m) Mass (m/z): 348 (M$^+$)

PREPARATION 30

A solution of 2-acetoxy-5-(1-benzylpiperidin-4-yl)-1-hydroxyiminopentylamine (0.59 g) in tetrahydrofuran (5 ml) was added dropwise to a solution of 4-nitrobenzoyl chloride (0.29 g) in tetrahydrofuran (5 ml) and the mixture was stirred overnight at ambient temperature and extracted with ethyl acetate. The extract was washed with a sodium hydrogencarbonate aqueous solution and water, dried over magnesium sulfate and evaporated in vacuo to give 2-acetoxy-5-(1-benzylpiperidin-4-yl)-1-(4-nitrobenzoyloxyimino)pentylamine (0.35 g).

mp: 149°–150° C. IR (Film): 3450, 3350, 1720, 1630, 1600 cm$^{-1}$ NMR (DMSO-d$_6$, δ): 1.10–1.30 (7H, m), 1.58–1.63 (2H, m), 1.77–1.94 (4H, m), 2.08 (3H, s), 2.74–2.79 (2H, m), 3.42 (2H, s), 5.09 (1H, t, J=7.0 Hz), 6.86 (2H, s), 7.22–7.30 (5H, m), 8.30 (2H, d, J=9.1 Hz), 8.37 (2H, d, J=9.1 Hz)

Elemental Analysis Calcd. for C$_{26}$H$_{32}$N$_4$O$_6$: C 62.88, H 6.49, N 11.28 Found: C 62.68, H 6.41, N 11.14 Mass (m/z): 497 (M$^+$+1)

PREPARATION 31

(1) A mixture of N-ethoxalyl-N'-(4-methylphenyl)hydrazine (3 g) and phosphorus pentoxide (9 g) in toluene (45 ml) was refluxed for 1 hour with stirring. After being cooled to room temperature, the reaction mixture was poured into a mixture of ice-water (50 ml) and ethyl acetate (50 ml). The organic layer was successively washed with a saturated sodium hydrogencarbonate aqueous solution and brine, dried over magnesium sulfate and evaporated in vacuo to afford 2-ethoxycarbonyl-5-(4-methylthiophenyl)-1,3,4-oxadiazole (1.89 g).

mp: 90°–92° C. IR (Nujol): 1745, 1600, 1180, 840 cm$^{-1}$ NMR (DMSO-d$_6$, δ): 1.37 (3H, t, J=7.1 Hz), 2.57 (3H, s), 4.46 (2H, q, J=7.1 Hz), 7.48 (2H, d, J=8.6 Hz), 7.96 (2H, d, J=8.6 Hz) MASS (m/z): 264 (M$^+$)

Elemental Analysis Calcd. for C$_{12}$H$_{12}$N$_2$O$_3$S: C 54.53, H 4.57, N 10.59 Found: C 54.68, H 4.49, N 10.51

The following compounds were obtained according to a similar manner to that of Preparation 31-(1).

(2) 2-Ethoxycarbonyl-5-{(E)-2-(4-cyanophenyl)vinyl}-1,3,4-oxadiazole mp: 182°–183° C. IR (Nujol): 2220, 1730, 1180 cm$^{-1}$ NMR (DMSO-d$_6$, δ): 1.37 (3H, t, J=7.1 Hz), 4.45 (2H, q, J=7.1 Hz), 7.60 (2H, d, J=16.5 Hz), 7.83 (2H, d, J=16.5Hz), 7.92 (2H, d, J=8.4 Hz), 8.05 (2H, d, J=8.4Hz)

(3) 2-Ethoxycarbonyl-5-(4-nitrophenyl)-1,3,4-oxadiazole mp: 148°–149° C. IR (Nujol): 1735, 1520, 1340, 1200 cm$^{-1}$ NMR (DMSO-d$_6$, δ): 1.39 (3H, t, J=7.1 Hz), 4.49 (2H, q, J=7.1 Hz), 8.35 (2H, d, J=8.9 Hz), 8.44 (2H, d, J=8.9 Hz)

PREPARATION 32

(1) To a solution of 2-ethoxycarbonyl-5-(4-methylthiophenyl)-1,3,4-oxadiazole (0.7 g) in chloroform (14 ml), m-chloroperoxybenzoic acid (0.57 g) was added dropwise at 4°–6° C. with stirring. After 30 minutes, the reaction mixture was extracted with chloroform (50 ml), washed with a sodium iodide aqueous solution, a sodium thiosulfate aqueous solution, a sodium hydrogencarbonate aqueous solution and brine successively and dried over magnesium sulfate. After evaporating the solvent, the residue was crystallized from diethyl ether to afford 2-ethoxycarbonyl-5-(4-methylsulfinylphenyl)-1,3,4-oxadiazole.

mp: 129°–131° C. IR (Nujol): 1745, 1190, 1050 cm$^{-1}$ NMR (DMSO-d$_6$, δ): 1.39 (3H, t, J=7.1 Hz), 2.85 (3H, s), 4.48 (2H, q, J=7.1 Hz), 7.95 (2H, d, J=8.5 Hz), 8.24 (2H, d, J=8.5 Hz) Mass (m/z): 280 (M$^+$)

Elemental Analysis Calcd. for C$_{12}$H$_{12}$N$_2$O$_4$S: C 51.42, H 4.31, N 9.99 Found: C 51.61, H 4.37, N 9.97

The following compound was obtained according to a similar manner to that of Preparation 32-(1).

(2) 2-Ethoxycarbonyl-5-(4-mesylphenyl)-1,3,4-oxadiazole mp: 177°–178° C. IR (Nujol): 1740, 1300, 1200, 850 cm$^{-1}$ NMR (DMSO-d$_6$, δ): 1.38 (3H, t, J=7.1 Hz), 3.33 (3H, s), 4.48 (2H, q, J=7.1 Hz), 8.18 (2H, d, J=8.0 Hz), 8.33 (2H, d, J=8.0 Hz) Mass (m/z): 296 (M$^+$)

Elemental Analysis Calcd. for C$_{12}$H$_{12}$N$_2$O$_5$S: C 48.64, H 4.08, N 9.45 Found: C 48.70, H 4.06, N 9.41

EXAMPLE 1

A mixture of 3-ethoxycarbonyl-5-(quinuclidin-3-yl)-1,2,4-oxadiazole (0.2 g) and 1-benzyl-4-(2-aminoethyl)piperidine (0.26 g) was stirred and heated at 100° C. for 2 hours. The cooled mixture was chromatographed on alumina eluting with chloroform to give 5-(quinuclidin-3-yl)-3-[{2-(1-benzylpiperidin-4-yl)ethyl}carbamoyl]-1,2,4-oxadiazole as an oil. The compound was treated with an ethanol solution of hydrogen chloride, the solution was evaporated in vacuo and the residue was powdered with ether to give 5-(quinuclidin-3-yl)-3-[{2-(1-benzylpiperidin-4-yl)ethyl}carbamoyl]-1,2,4-oxadiazole dihydrochloride (0.2 g).

mp: 210° C. (dec.) IR (Film): 3400, 1670, 1560 cm$^{-1}$ NMR (DMSO-d$_6$, δ): 1.50–1.85 (9H, m), 2.85–3.04 (3H, m), 3.24–3.91 (13H, m), 4.22, 4.25 (total 2H, s), 7.43–7.46 (3H, m), 7.60–7.63 (2H, m), 9.07 (1H, t, J=6 Hz), 10.83 (1H, br), 11.09 (1H, br) Mass (M/z): 423 (M$^+$ of free compound)

EXAMPLE 2

To a suspension of sodium hydride (0.4 g) in N,N-dimethylformamide was added 3-amino-5-(quinuclidin-3-yl)-1,2,4-oxadiazole (0.2 g) at 0° C. and the mixture was stirred for 1 hour. To the mixture was added (1-benzylpiperidin-4-yl)acetyl chloride hydrochloride (2.53 g) during 30 minutes at 0° C. After stirred for additional 1 hour. The mixture was quenched with water and extracted with ethyl acetate. The extract was washed with water, brine, dried over magnesium sulfate and evaporated in vacuo. The residue was purified by column chromatography on alumina with chloroform to give 3-{(1-benzylpiperidin-4-yl)acetylamino}-5-(quinuclidin-3-yl)-1,2,4-oxadiazole (0.11 g).

mp: 133°–134° C. IR (Nujol): 1690, 1610, 1550, 1535 cm$^{-1}$ NMR (CDCl$_3$, δ): 1.28–1.47 (4H, m), 1.73–1.78 (5H, m), 1.93–2.05 (3H, m), 2.25–2.30 (3H, m), 2.79–3.03 (5H, m), 3.13–3.18 (3H, m), 3.49 (2H, s), 4.07–4.12 (1H, m), 7.23–7.32 (5H, m) Mass (M/Z): 411 (M⁺)

Elemental Analysis Calcd. for $C_{23}H_{31}N_5O_2 \cdot 0.2H_2O$: C 66.86, H 7.66, N 16.95 Found: C 66.74, H 7.67, N 16.96

EXAMPLE 3

The following compounds were obtained according to similar manner to that of Example 1.

(1) 3-[{2-(1-Methylpiperidin-4-yl)ethyl}carbamoyl]-5-quinuclidin-3-yl)-1,2,4-oxadiazole mp: 141°–142° C. IR (Nujol): 3150, 1680, 1540 cm⁻¹ NMR (DMSO-d₆, δ): 1.09–1.84 (13H, m), 2.11 (3H, s), 2.16–2.17 (1H, m), 2.68–2.81 (6H, m), 3.17–3.33 (5H, m), 8.93 (1H, m) Mass (m/z): 347 (M⁺)

Elemental Analysis Calcd. for $C_{18}H_{29}N_5O_2$: C 62.22, H 8.41, N 20.15 Found: C 62.11, H 8.67, N 20.09

(2) 3-[{4-(1-Benzylpiperidin-4-yl)butyl}carbamoyl]-5-(quinuclidin-3-yl)-1,2,4-oxadiazole dihydrochloride IR (Film): 3300, 1680, 1540 cm⁻¹ NMR (DMSO-d₆, δ): 1.23–2.02 (16H, m) 2.82–3.23 (2H, m), 3.27–3.39 (6H, m), 3.60–3.92 (3H, m), 4.22–4.45 (4H, m), 7.42–7.44 (3H, m), 7.63–7.65 (2H, m), 9.05 (1H, t, J=6.0 Hz) Mass (m/z): 451 (M⁺ of free compound)

EXAMPLE 4

A mixture of 3-ethoxycarbonyl-5-(quinuclidin-3-yl)-1,2,4-oxadiazole (0.3 g) and 4-amino-1-benzylpiperidine (0.3 ml) was heated at 100° C. for 1 hour. After cooling to room temperature, the mixture was chromatographed on alumina eluting with 5% methanol-chloroform and treated with an ethanol solution of hydrogen chloride to give 3-{(1-benzylpiperidin-4-yl)carbamoyl}-5-(quinuclidin-3-yl)-1,2,4-oxadiazole dihydrochloride (0.15 g) as an oil.

IR (Film): 3300, 1680, 1540 cm⁻¹ NMR (DMSO-d₆, δ): 1.71–2.08 (7H, m), 3.05–3.11 (2H, m), 3.29–3.33 (5H, m), 3.61–3.73 (2H, m), 3.79–3.97 (2H, m), 4.26–4.42 (5H, m), 7.44–7.47 (3H, m), 7.67–7.77 (2H, m), 9.29 (1H, d, J=7.5 Hz) Mass (m/z): 395 (M⁺ of free compound)

EXAMPLE 5

(1) A mixture of 4-(1-benzylpiperidin-4-yl)butanamide oxime (1.0 g), sodium hydride (0.15 g) and molecular sieves 4A (2.0 g) in tetrahydrofuran (50 ml) was stirred at ambient temperature for 30 minutes. To the mixture was added dropwise a solution of methyl 3-quinuclidine carboxylate (0.49 g) in tetrahydrofuran (10 ml) and refluxed for 6 hours. After cooling to room temperature, the mixture was poured into water and extracted with ethyl acetate. The extracts were successively washed with water and brine, dried over magnesium sulfate and evaporated in vacuo. The residue was chromatographed on alumina eluting with chloroform to give 3-[3-(1-benzylpiperidin-4-yl)propyl]-5-(quinuclidin-3-yl)-1,2,4-oxadiazole (0.5 g) as an oil.

IR (Film): 1570, 1490 cm⁻¹ NMR (CDCl₃, δ): 1.26–1.93 (16H, m), 2.70 (2H, t, J=7.4 Hz), 2.83–2.94 (6H, m), 3.10–3.41 (3H, m), 3.47 (2H, s), 7.23–7.32 (5H, m) Mass (m/z): 394 (M⁺)

The following compound was obtained according to a similar manner to that of Example 5-(1).

(2) 3-[3-(1-Methylpiperidin-4-yl)propyl]-5-(quinuclidin-3-yl)-1,2,4-oxadiazole

IR (Film): 3350, 1570 cm⁻¹ NMR (CDCl₃, δ): 1.25–1.89 (16H, m), 2.26 (3H, s), 2.71 (2H, t, J=7.2 Hz), 2.80–2.94 (6H, m), 3.12–3.41 (3H, m) Mass (m/z): 318 (M⁺)

EXAMPLE 6

(1) A mixture of 3-ethoxycarbonyl-5-(4-nitrophenyl)-1,2,4-oxadiazole (1 g) and 4-(2-aminoethyl)-1-benzylpiperidine (0.83 g) was heated at 130° C. for 1 hour. After cooling to room temperature, the residue was subjected to column chromatography on silica gel using chloroform-methanol (20:1) as an eluent. The fractions containing the object compound were combined and evaporated. The residue was dissolved in ethanol, added to fumaric acid (0.22 g) and recrystallized to afford 3-[{2-(1-benzylpiperidin-4-yl)ethyl}carbamoyl]-5-(4-nitrophenyl)-1,2,4-oxadiazole fumarate (0.89 g).

mp: 224°–225° C. (dec.) IR (Nujol): 3275, 1670, 1525, 1345 cm⁻¹ NMR (DMSO-d₆, δ): 1.1–1.6 (5H, m), 1.65–1.8 (2H, m), 2.0–2.3 (2H, m), 2.8–3.0 (2H, m), 3.3–3.5 (2H, m), 3.64 (2H, s), 6.59 (2H, s), 7.2–7.4 (5H, m), 8.40 (2H, d, J=6.9 Hz), 8.48 (2H, d, J=6.9 Hz), 9.15 (1H, t, J=5.7 Hz)

Elemental Analysis Calcd. for $C_{27}H_{29}N_5O_8$: C 58.79, H 5.29, N 12.69 Found: C 58.51, H 5.38, N 12.69

The following compounds were obtained according to a similar manner to that of Example 6-(1).

(2) 3-[{2-(1-Benzylpiperidin-4-yl)ethyl}carbamoyl]-5-(4-methoxyphenyl)-1,2,4-oxadiazole fumarate mp: 213°–214° C. (dec.) IR (Nujol): 3320, 1670, 1605 cm⁻¹ NMR (DMSO-d₆, δ): 1.2–1.6 (5H, m), 1.7–1.9 (2H, m), 2.3–2.5 (2H, m), 2.9–3.2 (2H, m), 3.3–3.5 (2H, m), 3.82 (2H, s), 3.89 (3H, s), 6.60 (2H, s), 7.20 (2H, d, J=8.9 Hz), 7.3–7.5 (5H, m), 8.09 (2H, d, J=8.9 Hz), 9.03 (1H, t, J=5.6 Hz)

Elemental Analysis Calcd. for $C_{28}H_{32}N_4O_7$: C 62.67, H 6.01, N 10.44 Found: C 62.68, H 6.08, N 10.40

(3) 3-[{2-(1-Benzylpiperidin-4-yl)ethyl}carbamoyl]-5-(3-nitrophenyl)-1,2,4-oxadiazole fumarate mp: 196°–198° C. IR (Nujol): 3340, 1680, 1340, 980 cm⁻¹ NMR (DMSO-d₆, δ): 1.1–1.6(5H, m), 1.6–1.8 (2H, m), 2.0–2.2 (2H, m), 2.9–3.0 (2H, m), 3.3–3.4 (2H, m), 3.65 (2H, s), 6.59 (2H, s), 7.3–7.4 (5H, m), 7.9–8.0 (1H, m), 8.5–8.6 (2H, m), 8.84–8.86 (1H, m), 9.16 (1H, t, J=5.3 Hz)

Elemental Analysis Calcd. for $C_{27}H_{29}N_5O_8$: C 58.79, H 5.29, N 12.69 Found: C 58.63, H 5.12, N 12.59

(4) 3-[{2-(1-Benzylpiperidin-4-yl)ethyl}carbamoyl]-5-phenyl-1,2,4-oxadiazole fumarate mp: 218°–219° C. (dec.) IR (Nujol): 3290, 1670, 1550 cm⁻¹ NMR (DMSO-d₆, δ): 1.1–1.6 (5H, m), 1.7–1.8 (2H, m), 2.1–2.4 (2H, m), 2.9–3.1 (2H, m), 3.2–3.45 (2H, m), 3.70 (2H, s), 6.59 (2H, s), 7.3–7.4 (5H, m), 7.6–7.8 (3H, m), 8.1–8.2 (2H, m), 9.07 (1H, t, J=5.7 Hz)

(5) 3-[{2-(1-Benzylpiperidin-4-yl)ethyl}carbamoyl]-5-(4-methylphenyl)-1,2,4-oxadiazole fumarate mp: 219°–220° C. (dec.). IR (Nujol): 3250, 1670, 830 cm⁻¹ NMR (DMSO-d₆, δ): 1.1–1.6 (5H, m), 1.65–1.8 (2H, m), 2.1–2.3 (2H, m), 2.43 (3H, s), 2.9–3.05 (2H, m), 3.3–3.4 (2H, m), 3.69 (2H, s), 6.59 (2H, s), 7.2–7.4 (5H, m), 7.48 (2H, d, J=8.1 Hz), 8.03 (2H, d, J=8.1 Hz), 9.03 (1H, t, J=5.8 Hz)

(6) 3-[{2-(1-Benzylpiperidin-4-yl)ethyl}carbamoyl]-5-(4-trifluoromethylphenyl)-1,2,4-oxadiazole fumarate mp: 200°–201° C. IR (Nujol): 3300, 1710, 1670, 1600 cm⁻¹ NMR (DMSO-d₆, δ): 1.21–1.51 (5H, m), 1.71–1.76

(2H, m), 2.12–2.23 (2H, m), 2.90–2.96 (2H, m), 3.32–3.50 (2H, m), 6.59 (2H, s), 7.28–7.34 (5H, m), 8.05 (2H, d, J=8.3 Hz), 8.37 (2H, d, J=8.3 Hz), 9.13 (1H, t, J=5.7 Hz) Mass (m/z): 458 ($M^+$ of free compound)

Elemental Analysis Calcd. for $C_{28}H_{29}F_3N_4O_6$: C 58.53, H 5.08, N 9.75 Found: C 58.51, H 5.14, N 9.65

(7) 3-[{2-(1-Benzylpiperidin-4-yl)ethyl}carbamoyl]-5-(4-methylthiophenyl)-1,2,4-oxadiazole fumarate mp: 199°–201° C. (dec.) IR (Nujol): 3320, 1710, 1670, 970 cm$^{-1}$ NMR (DMSO-$d_6$, δ): 1.1–1.6 (5H, m), 1.65–1.8 (2H, m), 2.1–2.35 (2H, m), 2.58 (3H, s), 2.9–3.1 (2H, m), 3.2–3.4 (2H, m), 3.74 (2H, s), 6.59 (2H, s), 7.3–7.5 (5H, m), 7.51 (2H, d, J=8.6 Hz), 8.04 (2H, d, J=8.6 Hz), 9.04 (1H, t, J=5.8 Hz)

Elemental Analysis Calcd. for $C_{28}H_{32}N_4O_6S$: C 60.85, H 5.83, N 10.13 Found: C 60.84, H 5.75, N 10.09

(8) 3-[{2-(1-Benzylpiperidin-4-yl)ethyl}carbamoyl]-5-(pyridin-3-yl)-1,2,4-oxadiazole fumarate mp: 190°–191° C. IR (Nujol): 3300, 1710, 1670, 1600 cm$^{-1}$ NMR (DMSO-$d_6$, δ): 1.06–1.34 (5H, m), 1.73–1.78 m), 2.19–2.29 (2H, m), 2.51 (2H, br), 2.94–3.00 (2H, m), 3.32–3.35 (2H, m), 3.73 (2H, s), 6.59 (2H, s), 7.36 (5H, m), 7.71 (1H, dd, J=4.9, 8.0 Hz), 8.52 (1H, d, J=8.0 Hz), 8.90 (1H, d, J=4.9 Hz), 9.12 (1H, br), 9.31 (1H, s) Mass (m/z): 391 ($M^+$ of free compound)

(9) 5-[{2-(1-Benzylpiperidin-4-yl)ethyl}carbamoyl]-3-(4-nitrophenyl)-1,2,4-oxadiazole fumarate mp: 235°–237° C. (dec.) IR (Nujol): 3250, 1680, 1345, 720 cm$^{-1}$ NMR (DMSO-$d_6$, δ): 1.1–1.6 (5H, m), 1.6–1.8 (2H, m), 2.1–2.3 (2H, m), 2.8–3.0 (2H, m), 3.2–3.4 (2H, m), 3.68 (2H, m), 6.59 (2H, m), 7.2–7.4 (5H, m), 8.31 (2H, d, J=7 Hz), 8.45 (2H, d, J=7 Hz), 9.55 (1H, t, J=5.7 Hz)

EXAMPLE 7

(1) To a solution of 3-ethoxycarbonyl-5-(4-methylthiophenyl)-1,2,4-oxadiazole (0.8 g) in chloroform (16 ml), m-chloroperbenzoic acid (0.65 g) was added portionwise at 4°–6° C. with stirring. After 30 minutes, the reaction mixture was extracted with chloroform (50 ml), washed with an aqueous sodium iodide solution, an aqueous sodium thiosulfate solution, an aqueous sodium hydrogencarbonate solution and brine successively and dried over magnesium sulfate. After evaporating the solvent, to the residue was added 4-(2-aminoethyl)-1-benzylpiperidine (0.63 g) and the mixture was heated at 130° C. for 1 hour. The following procedures were employed according to a similar manner to that of Example 6-(1) to afford 3-[{2-(1-benzylpiperidin-4-yl)ethyl}carbamoyl]-5-(4-methylsulfinylphenylyl)-1,2,4-oxadiazole fumarate (0.97 g).

mp: 202°–203° C. (dec.) IR (Nujol): 3325, 1675, 1540 cm$^{-1}$ NMR (DMSO-$d_6$, δ): 1.2–1.6 (5H, m), 1.6–1.8 (2H, m), 2.1–2.3 (2H, m), 2.85 (3H, s), 2.9–3.1 (2H, 3.2–3.4 (2H, m), 3.68 (2H, s), 6.59 (2H, s), 7.2–7.4 (5H, m), 7.98 (2H, d, J=6.8 Hz), 8.32 (2H, d, J=6.8 Hz), 9.10 (1H, t, J=5.8 Hz)

The following compound was obtained according to a similar manner to that of Example 7-(1).

(2) 3-[{2-(1-Benzylpiperidin-4-yl)ethyl}carbamoyl]-5-(4-methylsulfonylphenyl)-1,2,4-oxadiazole ½ fumarate mp: 171°–174° C. (dec.) IR (Nujol): 3330, 1670, 1150 cm$^{-1}$ NMR (DMSO-$d_6$, δ): 1.1–1.6 (5H, m), 1.6–1.8 (2H, m), 1.9–2.2 (2H, m), 2.75–2.95 (2H, m), 3.2–3.4 (2H, m), 3.35 (3H, s), 3.58 (2H, s), 6.57 (1H, s), 7.2–7.4 (5H, m), 8.22 (2H, d, J=8.6 Hz), 8.40 (2H, d, J=8.6 Hz), 9.14 (1H, t, J=5, 8 Hz)

EXAMPLE 8

A suspension of 5-(1-benzylpiperidin-4-yl)-1-hydroxyiminopentylamine (1.0 g) and molecular sieves 3A (2.0 g) in tetrahydrofuran (50 ml) was stirred at ambient temperature for 30 minutes and then sodium hydride (0.14 g) was added thereto. After 30 minutes, a solution of ethyl 4-methoxybenzoate (0.56 g) in tetrahydrofuran was added to the mixture over 5 minutes. The mixture was heated under reflux overnight. After cooling, the reaction was filtered and the solvent was removed in vacuo. The residue was partitioned between ethyl acetate and water. The extract was washed with brine, dried over magnesium sulfate and removed in vacuo. The residue was chromatographed on silica gel eluting with chloroform/methanol (95:5) and the fractions containing the object compound were combined and evaporated. The residue was dissolved in ethanol (5 ml), added to fumaric acid (0.31 g) and recrystallized to afford 3-[4-(1-benzylpiperidin-4-yl)butyl]-5-(4-methoxyphenyl)-1,2,4-oxadiazole fumarate (1.01 g).

mp: 151°–152° C. IR (Nujol): 1690, 1640, 1610, 1560, 1520 cm$^{-1}$ NMR (DMSO-$d_6$, δ): 1.03–1.26 (7H, m), 1.63–1.69 (4H, m), 2.21 (2H, t, J=11.2 Hz), 2.73 (2H, t, J=8.0 Hz), 2.93 (2H, d, J=11.4 Hz), 3.70 (2H, s), 3.87 (3H, s), 6.59 (2H, s), 7.15 (2H, d, J=10.0 Hz), 7.29–7.37 (5H, m), 8.03 (2H, d, J=10.0 Hz) Mass (m/z): 405 ($M^+$)

EXAMPLE 9

To a solution of 3-[{2-(1-benzylpiperidin-4-yl)ethyl}carbamoyl-5-(4-nitrophenyl)-1,2,4-oxadiazole (1 g) in N,N-dimethylformamide (10 ml) was added sodium hydride (0.1 g) under ice cooling. After stirring for 30 minutes, methyl iodide (0.41 g) was added to this solution and the mixture was stirred for 1 hour. The mixture was quenched with an aqueous ammonium chloride solution and extracted with ethyl acetate (50 ml). The extract was successively washed with water and brine, dried over magnesium sulfate and evaporated in vacuo. The residue was column chromatographed on silica gel (150 ml) with chloroform/methanol=25/1 as an eluent. The fractions containing the object compound were combined and evaporated in vacuo. The residue was dissolved in ethanol (10 ml) and added to fumaric acid (0.13 g) in ethanol (10 ml). The crystalline residue was collected and dried in vacuo to afford 3-[N-{2-(1-benzylpiperidin-4-yl)ethyl}-N-methylcarbamoyl]-5-(4-nitrophenyl)-1,2,4-oxadiazole fumarate (0.53 g).

mp: 124°–125° C. (dec.) IR (Nujol): 3550, 3440, 1720, 1640, 1180 cm$^{-1}$ NMR (DMSO-$d_6$, δ): 1.0–1.8 (7H, m), 2.0–2.3 (2H, m), 2.7–3.1 (2H, m), 3.05 (3H, s), 3.3–3.7 (2H, m), 3.61, 3.69 (total 2H, each s), 6.59 (2H, s), 7.2–7.5 (5H, m), 8.41 (2H, d, J=8.8 Hz), 8.46 (2H, d, J=8.8 Hz)

EXAMPLE 10

(1) To a mixture of 3-[{2-(piperidin-4-yl)ethyl}carbamoyl]-5-(4-cyanophenyl)-1,2,4-oxadiazole hydrochloride (0.7 g), 4-fluorobenzaldehyde (0.24 g) and molecular sieves 4A (1.0 g) in methanol (7 ml) was added 1M solution of potassium hydroxide in methanol (1.93 ml). After stirring for 5 hours at ambient temperature, sodium borohydride (73 mg) was added to the mixture under ice cooling. The mixture was stirred for 20 minutes and evaporated in vacuo. The residue was dissolved in ethyl acetate and washed with water, brine, dried over magnesium sulfate and evaporated in vacuo to give a residue containing 3-[[2-{1-(4-fluorobenzyl)piperidin-4-yl}ethyl]carbamoyl]-5-(4-cyanophenyl)-1,2,4-oxadiazole. The residue and fumaric acid (0.11 g) were dissolved in hot ethanol (10 ml) and recrystallized to afford 3-[[2-{1-(4-fluorobenzyl)piperidin-4-yl}ethyl]carbamoyl]- 5-(4-cyanophenyl)-1,2,4-oxadiazole fumarate (0.50 g).

mp: 233°–235° C. (dec.) IR (Nujol): 3280, 2230, 1720, 1670 cm$^{-1}$ NMR (DMSO-d$_6$, δ): 1.19–1.29 (5H, m), 1.47–1.51 (2H, m), 2.07–2.18 (2H, m), 2.87–2.92 (2H, m), 3.31–3.34 (2H, m), 3.62 (2H, s), 6.59 (2H, 7.16 (2H, dd, J=8.5, 8.5 Hz), 7.38 (2H, dd, J=5.7, 8.5 Hz), 8.14 (2H, d, J=8.4 Hz), 8.31 d, J=8.4 Hz), 9.12 (1H, m) Mass (m/z): 432 (M$^+$ of free compound)

Elemental Analysis Calcd. for C$_{24}$H$_{24}$FN$_5$O$_2$·C$_4$H$_4$O$_4$: C 61.19, H 5.13, N 12.74 Found: C 61.16, H 5.02, N 12.65

The following compounds were obtained according to a similar manner to that of Example 10-(1).

(2) 3-[[2-{1-(3-Fluorobenzyl)piperidin-4-yl}ethyl]carbamoyl]-5-(4-cyanophenyl)-1,2,4-oxadiazole fumarate mp: 251°–253° C. (dec.) IR (Nujol): 3300, 2230, 1710, 1675 cm$^{-1}$ NMR (DMSO-d$_6$, δ): 1.17–1.28 (3H, m), 1.48–1.51 (2H, m), 1.69–1.74 (2H, m), 2.00–2.11 (2H, m), 2.83–2.88 (2H, m), 3.31–3.43 (2H, m), 3.58 (2H, s), 6.60 (2H, s), 7.06–7.18 (3H, m), 7.32–7.43 (1H, m), 8.14 (2H, d, J=8.5 Hz), 8.31 (2H, d, J=8.5 Hz), 9.09–9.12 (1H, m) Mass (m/z): 433 (M$^+$ of free compound)

Elemental Analysis Calcd. for C$_{24}$H$_{24}$FN$_5$O$_2$·C$_4$H$_4$O$_4$: C 61.19, H 5.13, N 12.74 Found: C 61.11, H 5.11, N 12.62

(3) 3-[[2-{1-(2-Fluorobenzyl)piperidin-4-yl}ethyl]carbamoyl]-5-(4-cyanophenyl)-1,2,4-oxadiazole fumarate mp: 231°–232° C. IR (Nujol): 3300, 2230, 1710, 1680 cm$^{-1}$ NMR (DMSO-d$_6$, δ): 1.18–1.29 (3H, m), 1.47–1.50 (2H, m), 1.71–1.76 (2H, m), 2.14–2.24 (2H, m), 2.91–2.96 (2H, m), 3.29–3.36 (2H, m), 3.70 (2H, s), 6.60 (2H, s), 7.15–7.24 (2H, m), 7.33–7.48 (2H, m), 8.13 2H, d, J=8.5 Hz), 8.32 (2H, d, J=8.5 Hz) Mass (m/z): 433 (M$^+$ of free compound)

Elemental Analysis Calcd. for C$_{24}$H$_{29}$FN$_5$O$_2$·C$_4$H$_4$O$_4$: C 61.19, H 5.13, N 12.74 Found: C 61.29, H 5.07, N 12.65

(4) 3-[[2-{1-(4-Cyanobenzyl)piperidin-4-yl}ethyl]carbamoyl]-5-(4-cyanophenyl)-1,2,4-oxadiazole fumarate mp: 190°–191° C. IR (Nujol): 3300, 2210, 1670 cm$^{-1}$ NMR (DMSO-d$_6$, δ): 1.18–1.49 (5H, m), 1.69–1.74 (2H, m), 2.03–2.13 (2H, m), 2.81–2.87 (2H, m), 3.32–3.35 (2H, m), 3.65 (2H, m), 6.61 (2H, m), 7.53 (2H, d, J=7.8 Hz), 7.80 (2H, d, J=7.8 Hz), 8.14 (2H, d, J=8.2 Hz), 8.31 (2H, d, J=8.2 Hz), 9.08–9.12 (1H, m)

(5) 3-[[2-{1-(4-Chlorobenzyl)piperidin-4-yl}ethyl]carbamoyl]-5-(4-cyanophenyl)-1,2,4-oxadiazole fumarate mp: 216°–218° C. IR (Nujol): 3280, 2210, 1670 cm$^{-1}$ NMR (DMSO-d$_6$, δ): 1.09–1.50 (5H, m), 1.68–1.73 (2H, m), 1.98–2.09 (2H, m), 2.81–2.86 (2H, m), 3.31–3.34 (2H, m), 3.54 (2H, s), 6.60 (2H, s), 7.31–7.42 (4H, m), 8.14 (2H, d, J=8.5 Hz), 8.31 (2H, d, J=8.5 Hz), 9.08–9. 12 (1H, m)

Elemental Analysis Calcd. for C$_{24}$H$_{24}$ClN$_5$O$_2$·C$_4$H$_4$O$_4$: C 59.41, H 4.98, N 12.37 Found: C 59.03, H 5.03, N 12.37

(6) 3-[[2-{1-(4-Methoxybenzyl)piperidin-4-yl}ethyl]carbamoyl]-5-(4-cyanophenyl)-1,2,4-oxadiazole fumarate mp: 117°–119° C. IR (Nujol): 2210, 1680 cm$^{-1}$ NMR (DMSO-d$_6$, δ): 1.29–1.48 (5H, m), 1.72–1.77 (2H, m), 2.20–2.25 (2H, m), 2.95–3.00 (2H, m), 3.34–3.50 (2H, m), 3.69 (2H, s), 3.75 (3H, s), 6.57 (2H, s), 6.91 (1H, d, J=8.1 Hz), 7.28 (2H, d, J=8.1 Hz), 8.14 (2H, d, J=8.2 Hz), 8.31 (2H, d, J=8.2 Hz), 9.08–9.12 (1H, m)

(7) 3-[[2-{1-(4-Nitrobenzyl)piperidin-4-yl}ethyl]carbamoyl-5-(4-cyanophenyl)-1,2,4-oxadiazole fumarate mp: 217°–218 ° C. IR (Nujol): 3440, 3300, 2240, 1720, 1670 cm$^{-1}$ NMR (DMSO-d$_6$, δ): 1.18–1.51 (5H, m), 1.69–1.74 m), 2.00–2.10 (2H, m), 2.80–2.86 (2H, m), 3.32–3.35 (2H, m), 3.66 (2H, s), 6.62 (2H, s), 7.60 (2H, d, J=8.7 Hz), 8.14 (2H, d, J=8.5 Hz), 8.20 (2H, d, J=8.7 Hz), 8.32 (2H, d, J=8.5 Hz), 9.08–9.14 (1H, m) Mass (m/z): 460 (M$^+$ of free compound)

Elemental Analysis Calcd. for C$_{24}$H$_{24}$N$_6$O$_4$·C$_4$H$_4$O$_4$: C 58.32, H 4.89, N 14.57 Found: C 58.81, H 4.95, N 14.57

(8) 3-[[2-{1-(4-Methylbenzyl)piperidin-4-yl}ethyl]carbamoyl]-5-(4-cyanophenyl)-1,2,4-oxadiazole fumarate mp: 228°–229° C. IR (Nujol): 3300, 2240, 1720, 1670 cm$^{-1}$ NMR (DMSO-d$_6$, δ): 1.21–1.31 (5H, m), 1.47–1.50 (2H, m), 2.13–2.24 (2H, m), 2.29 (3H, s), 2.91–2.97 (2H, m), 3.31–3.34 (2H, m), 3.65 (2H, s), 6.58 (2H, s), 7.14 (2H, d, J=8.0 Hz), 7.23 (2H, d, J=8.0 Hz), 8.14 (2H, d, J=8.5 Hz), 8.31 (2H, d, J=8.5 Hz), 9.08–9.14 (1H, m)

EXAMPLE 11

The following compounds were obtained according to a similar manner to that of Example 6-(1).

(1) 3-[{2-(1-Benzylpiperidin-4-yl)ethyl}carbamoyl]-5-[(E)-2-(4-cyanophenyl)ethenyl]-1,2,4-oxadiazole fumarate mp: 209°–210° C. (dec.) IR (Nujol): 3300, 2225, 1680, 1640 cm$^{-1}$ NMR (DMSO-d$_6$, δ): 1.1–1.6 (5H, m), 1.6–1.8 (2H, m), 2.0–2.2 (2H, m), 2.8–3.0 (2H, m), 3.2–3.4 (2H, m), 3.62 (2H, s), 6.59 (2H, s), 7.33 (5H, m), 7.62 (2H, d, J=16.4 Hz), 7.96 (2H, d, J=8.5 Hz), 7.80 (2H, d, J=16.4 Hz), 8.05 (2H, d, J=8.5 Hz), 9.03 (1H, t, J=5.7 Hz)

Elemental Analysis Calcd. for C$_{26}$H$_{27}$N$_5$O$_2$·C$_4$H$_4$O$_4$: C 64.62, H 5.60, N 12.55 Found: C 64.68, H 5.58, N 12.56

(2) 2-[{2-(1-Benzylpiperidin-4-yl)ethyl}carbamoyl]-5-[(E)-2-(4-cyanophenyl)ethenyl]-1,3,4-oxadiazole fumarate mp: 214°–215° C. (dec.) IR (Nujol): 3285, 2225, 1710, 1690 cm$^{-1}$ NMR (DMSO-d$_6$, δ): 1.1–1.6 (5H, m), 1.6–1.8 (2H, m), 2.1–2.3 (2H, m), 2.8–3.0 (2H, m), 3.2–3.4 (2H, m), 3.66 (2H, s), 6.59 (2H, s), 7.33 (5H, s), 7.62 (2H, d, J=16.5 Hz), 7.79 (2H, d, J=16.5 Hz), 7.93 (2H, d, J=8.5 Hz), 8.02 (2H, d, J=8.5 Hz), 9.34 (1H, t, J=5.8 Hz)

(3) 5-(4-Acetylphenyl)-3-[{2-(1-benzylpiperidin-4-yl)ethyl}carbamoyl]-1,2,4-oxadiazole fumarate mp: 197°–198° C. IR (Nujol): 3325, 1680 cm$^{-1}$ NMR (DMSO-d$_6$, δ): 1.10–1.60 (5H, m), 1.70–1.95 (2H, m), 2.10–2.35 (2H, m), 2.67 (3H, s), 2.90–3.10 (2H, m), 3.30–3.45 (2H, m), 3.72 (2H, s), 6.59 (2H, s), 7.30–7.40 (5H, m), 8.19 (2H, d, J=8.6 Hz), 8.28 (2H, d, J=8.6 Hz), 9.13 (1H, t, J=5.8 Hz)

Elemental Analysis Calcd. for C$_{25}$H$_{28}$N$_4$O$_3$·C$_4$H$_4$O$_4$: C 63.49, H 5.87, N 10.21 Found: C 63.47, H 6.08, N 10.13

(4) 3-[{2-(1-Benzylpiperidin-4-yl)ethyl}carbamoyl]-5-(4-cyanophenyl)-1,2,4-oxadiazole fumarate mp: 235°–236° C. (dec.) IR (Nujol): 3280, 2230, 1680 cm$^{-1}$ NMR (DMSO-d$_6$, δ): 1.10–1.60 (5H, m), 1.70–1.80 (2H, m), 2.10–2.30 (2H, m), 2.90–3.05 (2H, m), 3.30–3.40 (2H, m), 3.70 (2H, s), 6.58 (2H, s), 7.30–7.40 (5H, m), 8.14 (2H, d, J=6.8 Hz), 8.31 (2H, d, J=6.8 Hz), 9.13 (1H, t, J=5.7 Hz)

(5) 3-[{2-(1-Benzylpiperidin-4-yl)ethyl}carbamoyl]-5-[(E)-2-(4-nitrophenyl)ethenyl]-1,2,4-oxadiazole hydrochloride mp: 234°–236° C. (dec.) IR (Nujol): 3230, 1685, 1340 cm$^{-1}$ NMR (DMSO-d$_6$, δ): 1.40–2.00 (7H, m), 2.6–3.5 (6H, m), 4.23 (2H, s), 7.4–7.5 (3H, m), 7.62 (2H, s), 7.67 (1H, d, J=16.4 Hz), 8.06 (1H, d, J=16.4 Hz), 8.14 (2H, d, J=8.9 Hz), 8.30 (2H, d, J=8.9 Hz), 9.10 (1H, t, J=5.7 Hz), 10.90 (1H, br)

(6) 3-[{2-(1-Benzylpiperidin-4-yl)ethyl}carbamoyl]-5-[(4-nitrophenyl)methyl]-1,2,4-oxadiazol fumarate mp: 135°–136° C. IR (Nujol): 3320, 1685 cm$^{-1}$ NMR (DMSO-d$_6$, δ): 1.1–1.5 (5H, m), 1.6–1.8 (2H, m), 2.1–2.3 (2H, m), 2.8–3.0 (2H, m), 3.1–3.3 (2H, m), 3.70 (2H, s), 4.64 (2H, s), 6.59 (2H, s)

(7) 2-[{2-(1-Benzylpiperidin-4-yl)ethyl)carbamoyl]-5-(4-cyanophenyl)-1,3,4-oxadiazole fumarate mp: 188°–190° C. (dec.) IR (Nujol): 3310, 2230, 1710, 1685 cm$^{-1}$ NMR (DMSO-d$_6$, δ): 1.1–1.6 (5H, m), 1.6–1.8 (2H, m), 2.0–2.25 (2H, m), 2.8–3.0 (2H, m), 3.2–3.4 (2H, m), 3.65 (2H, s), 6.59 (2H, s), 7.34 (5H, s), 8.12 (2H, d, J=8.5 Hz), 8.24 (2H, d, J=8.5 Hz), 9.41 (1H, t, J=5.8 Hz)

Elemental Analysis Calcd. for C$_{28}$H$_{29}$N$_5$O$_6$: C 63.26, H 5.49, N 13.17 Found: C 63.26, H 5.49, N 13.19

(8) 2-[{2-(1-Benzylpiperidin-4-yl)ethyl}carbamoyl]-5-(4-nitrophenyl)-1,3,4-oxadiazole fumarate mp: 200°–201° C. (dec.) IR (Nujol): 3300, 1695, 1160 cm$^{-1}$ NMR (DMSO-d$_6$, δ): 1.1–1.6 (5H, m), 1.6–1.8 (2H, m), 2.1–2.3 (2H, m), 2.85–3.1 (2H, m), 3.2–3.4 (2H, m), 3.71 (2H, s), 6.58 (2H, s), 7.2–7.4 (5H, m), 8.34 (2H, d, J=8.9 Hz), 8.46 (2H, d, J=8.9 Hz), 9.44 (1H, t, J=5.7 Hz)

Elemental Analysis Calcd. for C$_{27}$H$_{29}$N$_5$O$_8$: C 58.79, H 5.29, N 12.69 Found: C 58.49, H 5.27, N 12.60

(9) 2-[{2-(1-Benzylpiperidin-4-yl)ethyl}carbamoyl]-5-(4-methylsulfonylphenyl)-1,3,4-oxadiazole hydrochloride mp: 180°–182° C. IR (Nujol): 3360, 1690, 1150 cm$^{-1}$ NMR (DMSO-d$_6$, δ): 1.40–2.00 (7H, m), 2.70–3.50 (6H, m), 3.33 (3H, s), 4.20–4.40 (2H, m), 7.40–7.55 (3H, m), 7.60–7.70 (2H, m), 8.19 (2H, d, J=8.5 Hz), 8.32 (2H, d, J=8.5 Hz), 9.51 (1H, t, J=5.8 Hz), 10.60–10.80 (1H, br).

(10) 2-[{2-(1-Benzylpiperidin-4-yl)ethyl}carbamoyl]-5-(4-methylsulfinylphenyl)-1,3,4-oxadiazole hydrochloride mp: 159°–161° C. IR (Nujol): 3325, 1580, 1050 cm$^{-1}$ NMR (DMSO-d$_6$, δ): 1.40–2.00 (7H, m), 2.83 (3H, m), 2.70–3.50 (6H, m), 4.20–4.40 (2H, m), 7.40–7.50 (3H, m), 7.55–7.70 (2H, m), 7.95 (2H, d, J=8.5 Hz), 8.25 (2H, d, J=8.5 Hz), 9.45 (1H, t, J=5.9 Hz), 10.50–10.80 (1H, br)

(11) 2-[{2-(1-Benzylpiperidin-4-yl)ethyl}carbamoyl]-5-(4-methylthiophenyl)-1,3,4-oxadiazole fumarate mp: 147°–148° C. (dec.) IR (Nujol): 1680, 1645, 1600 cm$^{-1}$ NMR (DMSO-d$_6$, δ): 1.20–1.60 (5H, m), 1.70–1.85 (2H, m), 2.10–2.30 (2H, m), 2.57 (3H, s), 2.90–3.00 (2H, m), 3.20–3.40 (2H, m), 3.69 (2H, s), 6.59 (2H, s), 7.30–7.40 (5H, m), 7.48 (2H, d, J=8.6 Hz), 7.98 (2H, d, J=8.6 Hz), 9.34 (1H, t, J=5.7 Hz)

EXAMPLE 12

A mixture of 3-ethoxycarbonyl-5-(4-cyanophenyl)-1,2,4-oxadiazole (2.0 g) and 2-(1-tert-butoxycarbonylpiperidin-4-yl)ethylamine in N,N-dimethylformamide (1 ml) was heated at 120° C. for 5 hours. The mixture was dissolved with ethyl acetate, washed with water, brine, dried over magnesium sulfate and evaporated in vacuo. The residue was recrystallized from ethanol to afford 3-[{2-(1-tert-butoxycarbonylpiperidin-4-yl)ethyl}carbamoyl]-5-(4-cyanophenyl)- 1,2,4-oxadiazole (2.6 g).

mp: 138°–139° C. IR (Nujol): 3260, 2230, 1685 cm$^{-1}$ NMR (DMSO-d$_6$, δ): 1.00–1.07 (2H, m), 1.39 (9H, s), 1.46–1.48 (3H, m), 1.66–1.71 (2H, m), 2.65–2.68 (2H, m), 3.32–3.34 (2H, m), 3.89–3.95 (2H, m), 8.14 (2H, d, J=8.4 Hz), 8.31 (2H, d, J=8.4 Hz), 9.10–9.16 (1H, m)

Elemental Analysis Calcd. for C$_{22}$H$_{27}$N$_5$O$_4$: C 62.10, H 6.39, N 16.45 Found: C 61.84, H 6.42, N 16.23

EXAMPLE 13

To a solution of 3-[{2-(1-tert-butoxycarbonylpiperidin-4-yl)ethyl}carbamoyl]-5-(4-cyanophenyl)-1,2,4-oxadiazole (2.5 g) in dioxane (30 ml) was added 4N hydrochloric acid in dioxane (13 ml) under ice cooling. After stirring for 5 hours at ambient temperature, the mixture was evaporated in vacuo. The residue was recrystallized from ethanol-ether to afford 3-[{2-(piperidin-4-yl)ethyl}carbamoyl]-5-(4-cyanophenyl)-1,2,4-oxadiazole hydrochloride (1.71 g).

mp: 257°–258° C. (dec.) IR (Nujol): 3250, 2230, 1680 cm$^{-1}$ NMR (DMSO-d$_6$, δ): 1.32–1.60 (5H, m), 1.82–1.89 (2H, m), 2.78–2.83 (2H, m), 3.20–3.49 (4H, m), 8.14 (2H, d, J=8.4 Hz), 8.32 (2H, d, J=8.4 Hz), 8.84–9.01 (2H, br), 9.18 (1H, m) Mass (m/z): 326 (M$^+$ of free compound)

EXAMPLE 14

The following compounds were obtained according to a similar manner to that of Example 6-(1).

(1) 3-{(1-Benzylpiperidin-4-yl)carbamoyl}-5-(4-nitrophenyl)- 1,2,4-oxadiazole fumarate mp: 244°–246° C. (dec.) IR (Nujol): 3230, 1700, 1680, 1650 cm$^{-1}$ NMR (DMSO-d$_6$, δ): 1.68–1.78 (4H, m), 2.15–2.25 (2H, m), 2.89–2.95 (2H, m), 3.60 (2H, s), 3.82–3.86 (1H, m), 6.61 (2H, s), 7.28–7.36 (5H, m), 8.40 (2H, d, J=9.2 Hz), 8.48 (2H, d, J=9.2 Hz), 9.11 (1H, d, J=8.0 Hz)

Elemental Analysis Calcd. for C$_{21}$H$_{21}$N$_5$O$_4$·C$_4$H$_4$O$_4$: C 57.35, H 4.81, N 13.37 Found: C 57.45, H 4.65, N 13.21

(2) 3-{(1-Benzylpiperidin-4-yl)methylcarbamoyl}-5-(4-nitrophenyl)-1,2,4-oxadiazole fumarate mp: 218°–220° C. (dec.) IR (Nujol): 3380, 1700, 1680 cm$^{-1}$ NMR (DMSO-d$_6$, δ): 1.26–1.31 (2H, m), 1.67–1.73 (3H, m), 2.12–2.23 (2H, m), 2.91–2.97 (2H, m), 3.18–3.25 (2H, m), 3.67 (2H, s), 6.59 (2H, s), 7.30–7.36 (5H, m), 8.40 (2H, d, J=9.0 Hz), 8.48 (2H, d, J=9.0 Hz), 9.17–9.21 (1H, m) Mass (m/z): 421 (M$^+$ of free compound)

(3) 3-[{3-(1-Benzylpiperidin-4-yl)propyl}carbamoyl]-5-(4-nitrophenyl)-1,2,4-oxadiazole fumarate mp: 204°–205° C. IR (Nujol): 3300, 1700, 1690 cm$^{-1}$ NMR (DMSO-d$_6$, δ): 1.20–1.30 (5H, m), 1.37–1.70 (4H, m), 2.12–2.22 (2H, m), 2.90–2.96 (2H, m), 3.26–3.29 (2H, m), 3.66 (2H, s), 6.58 (2H, s), 7.30–7.35 (5H, m), 8.40 (2H, d, J=9.1 Hz), 8.48 (2H, d, J=9.1 Hz), 9.13–9.17 (1H, m) Mass (m/z): 448 (M$^+$ of free compound−1)

(4) 3-[{2-(1-Benzylpiperidin-4-yl)ethyl}carbamoyl]-5-(2-nitrophenyl)- 1,2,4-oxadiazole fumarate mp: 230°–231° C. IR (Nujol): 3300, 1710, 1680 cm$^{-1}$ NMR (DMSO-d$_6$, δ): 1.17–1.50 (5H, m), 1.68–1.74 (2H, m), 2.04–2.14 (2H, m), 2.85–2.91 (2H, m), 3.30–3.39 (2H, m), 3.60 (2H, s), 6.59 (2H, s), 7.26–7.35 (5H, m), 7.99–8.06 (2H, m), 8.11–8.16 (1H, m), 8.27–8.32 (1H, m), 9.15 (1H, m) Mass (m/z): 434 (M$^+$ of free compound−1)

Elemental Analysis Calcd. for C$_{23}$H$_{25}$N$_5$O$_4$·C$_4$H$_4$O$_4$: C 58.79, H 5.29, N 12.69 Found: C 58.85, H 5.31, N 12.50

(5) 3-[{2-(1-Benzylpiperidin-4-yl)ethyl}carbamoyl]-5-(4-chlorophenyl)-1,2,4-oxadiazole fumarate mp: 220°–222° C. IR (Nujol): 3300, 1710, 1680 cm$^{-1}$ NMR (DNSO-d$_6$, δ): 1.24–1.48 (5H, m), 1.72–1.78 (2H, m), 2.19–2.24 (2H, m), 2.94–3.00 (2H, m), 3.28–3.34 (2H, m), 3.74 (2H, s), 6.59 (2H, s), 7.30–7.47 (5H, m), 7.75 (2H, d, J=8.8 Hz), 8.16 (2H, d, J=8.8 Hz), 9.09 (1H, m) Mass: (m/z): 426 (M+ of free compound)

Elemental Analysis Calcd. for $C_{23}H_{25}ClN_4O_2 \cdot C_4H_4O_4$: C 59.94, H 5.40, N 10.35 Found: C 59.81, H 5.39, N 10.22

(6) 3-[{2-(1-Benzylpiperidin-4-yl)ethyl}carbamoyl]-5-methyl-1,2,4-oxadiazole fumarate mp: 116°–118° C. (dec.) IR (Nujol): 3260, 1700, 1680 cm$^{-1}$ NMR (DMSO-d$_6$, δ): 1.17–1.43 (5H, m), 1.68–1.73 (2H, m), 2.10–2.20 (2H, m), 2.65 (3H, s), 2.89–2.94 (2H, m), 3.25–3.28 (2H, m), 3.66 (2H, s), 6.58 (2H, s), 7.25–7.35 (5H, m), 8.96 (1H, m)

(7) 3-[{2-(1-Benzylpiperidin-4-yl) ethyl}carbamoyl]-5-(4-pyridyl)-1,2,4-oxadiazole fumarate mp: 185°–186° C. IR (Nujol): 3330, 1700, 1660 cm$^{-1}$ NMR (DMSO-d$_6$, δ): 1.21–1.32 (5H, m), 1.48–1.51 (2H, m), 1.71–1.77 (2H, m), 2.91–2.97 (2H, m), 3.28–3.43 (2H, m), 3.69 (2H, s), 6.59 (2H, 7.29–7.35 (5H, m), 8.06 (2H, d, J=6.1 Hz), 8.91 (2H, d, J=6.1 Hz), 9.14 (1H, m) Mass (m/z): 390 (M+ of free compound–1)

(8) 3-[{2-(1-Benzylpiperidin-4-yl)ethyl}carbamoyl]-5-(4-fluorophenyl)-1,2,4-oxadiazole fumarate mp: 188°–190° C. IR (Nujol): 3260, 1700, 1670 cm$^{-1}$ NMR (DMSO-d$_6$, δ): 1.20–1.50 (5H, m), 1.71–1.76 (2H, m), 2.12–2.23 (2H, m), 2.90–2.96 (2H, m), 3.30–3.37 (2H, m), 3.67 (2H, s), 6.59 (2H, s), 7.28–7.35 (5H, m), 7.48–7.57 (2H, m), 8.19–8.26 (2H, m), 9.06 (1H, m) Mass (m/z): 407 (M+ of free compound–1)

(9) 3-[[2-{1-(3-Methoxybenzyl)piperidin-4-yl}ethyl]carbamoyl]-5-(4-nitrophenyl)-1,2,4-oxadiazole fumarate mp: 219°–221° C. IR (Nujol): 3280, 1700, 1670 cm$^{-1}$ NMR (DMSO-d$_6$, δ): 1.21–1.51 (5H, m), 1.70–1.76 (2H, m), 2.09–2.20 (2H, m), 2.89–2.95 (2H, m), 3.32–3.46 (2H, m), 3.62 (2H, s), 3.74 (3H, s), 6.59 (2H, s), 6.84–6.92 (3H, m), 7.22–7.30 (1H, m), 8.40 (2H, d, J=9.1 Hz), 8.48 (2H, d, J=9.1 Hz), 9.12–9.18 (1H, m) Mass (m/z): 464 (M+ of free compound–1)

Elemental Analysis Calcd. for $C_{24}H_{27}N_5O_5 \cdot C_4H_4O_4$: C 57.82, H 5.37, N 12.04 Found: C 57.75, H 5.46, N 11.95

(10) 3-[{2-(1-Benzylpiperazin-4-yl)ethyl}carbamoyl]-5-(4-nitrophenyl)-1,2,4-oxadiazole fumarate mp: 182°–184° C. IR (Nujol): 3200, 1685, 1620 cm$^{-1}$ NMR (DMSO-d$_6$, δ): 2.42–2.56 (7H, m), 3.41–3.44 (1H, m), 3.48 (2H, s), 3.80–4.10 (4H, br), 6.59 (1H, s), 7.24–7.33 (5H, m), 8.40 (2H, d, J=9.1 Hz), 8.49 (2H, d, J=9.1 Hz), 8.99–9.02 (1H, m) Mass (m/z): 436 (M+ of free compound)

(11) 3-[{2-(1-Benzylpiperidin-4-yl)ethyl}carbamoyl]-5-(2-cyanothiophen-5-yl)-1,2,4-oxadiazole fumarate mp: 204°–205° C. IR (Nujol): 3300, 2220, 1700, 1670 cm$^{-1}$ NMR (DMSO-d$_6$, δ): 1.23–1.49 (5H, m), 1.69–1.74 (2H, m), 2.05–2.20 (2H, m), 2.88–2.94 (2H, m), 3.29–3.32 (2H, m), 3.64 (2H, s), 6.59 (2H, s), 7.28–7.35 (5H, m), 8.19 (2H, s), 9.12–9.16 (1H, m) Mass (m/z): 422 (M+ of free compound+1)

Elemental Analysis Calcd. for $C_{22}H_{23}N_5O_2S \cdot C_4H_4O_4$: C 58.09, H 5.06, N 13.02 Found: C 58.19, H 5.00, N 12.88

(12) 3-[{2-(1-(4-Fluorobenzyl)piperidin-4-yl)ethyl}carbamoyl]-5-(4-pyridyl)-1,2,4-oxadiazole fumarate mp: 182°–183° C. IR (Nujol): 3260, 1700, 1670 cm$^{-1}$ NMR (DMSO-d$_6$, δ): 1.31–1.49 (5H, m), 1.74–1.91 (2H, m), 2.24–2.35 (2H, m), 2.96–3.02 (2H, m), 3.32–3.35 (2H, m), 3.77 (2H, s), 6.60 (2H, s), 7.19 (2H, dd, J=8.7, 8.7 Hz), 7.42 (2H, dd, J=5.7, 8.7 Hz), 8.07 (2H, d, J=5.8 Hz), 8.93 (2H, d, J=5.8 Hz), 9.15 (1H, m) Mass (m/z): 408 (M+ of free compound–1)

(13) 3-[[2-{1-(4-Fluorobenzyl)piperidin-4-yl}ethyl]carbamoyl]-5-(4-fluorophenyl)-1,2,4-oxadiazole fumarate mp: 188°–190° C. IR (Nujol): 3220, 1700, 1660 cm$^{-1}$ NMR (DMSO-d$_6$, δ): 1.23–1.48 (5H, m), 1.72–1.78 (2H, m), 2.17–2.80 (2H, m), 2.92–2.98 (2H, m), 3.31–3.44 (2H, m), 3.71 (2H, s), 6.59 (2H, s), 7.18 (2H, dd, J=8.8, 8.8 Hz), 7.40 (2H, dd, J=5.7, 8.8 Hz), 7.52 (2H, dd, J=8.8, 8.8 Hz), 8.23 (2H, dd, J=5.7, 8.8 Hz), 9.07 (1H, m) Mass (m/z): 425 (M+ of free compound–1)

Elemental Analysis Calcd. for $C_{23}H_{24}F_2N_4O_2 \cdot C_4H_4O_4$: C 59.77, H 5.20, N 10.32 Found: C 59.33, H 5.31, N 10.19

(14) 3-[[2-{1-(4-Fluorobenzyl)piperidin-4-yl}ethyl]carbamoyl]-5-(4-nitrophenyl)-1,2,4-oxadiazole fumarate mp: 215°–216° C. IR (Nujol): 3370, 1700, 1670 cm$^{-1}$ NMR (DMSO-d$_6$, δ): 1.17–1.51 (5H, m), 1.69–1.75 (2H, m), 2.02–2.13 (2H, m), 2.84–2.90 (2H, m), 3.31–3.34 (2H, m), 3.58 (2H, s), 6.59 (2H, s), 7.16 (2H, dd, J=8.8, 8.8 Hz), 7.37 (2H, dd, J=5.7, 8.8 Hz), 8.40 (2H, d, J=9.0 Hz), 8.49 (2H, d, J=9.0 Hz), 9.14 (1H, m) Mass (m/z): 453 (M+ of free compound)

Elemental Analysis Calcd. for $C_{23}H_{24}FN_5O_4 \cdot C_4H_4O_4$: C 56.93, H 4.95, N 12.29 Found: C 56.80, H 4.91, N 12.23

(15) 3-[[2-{1-(4-Fluorobenzyl)piperidin-4-yl}ethyl]carbamoyl]-5-(4-cyanophenyl)-1,2,4-oxadiazole fumarate mp: 233°–235° C. (dec.) IR (Nujol): 3280, 2230, 1720, 1670 cm$^{-1}$ NMR (DMSO-d$_6$, δ): 1.19–1.29 (5H, m), 1.47–1.51 (2H, m), 2.07–2.18 (2H, m), 2.87–2.92 (2H, m), 3.31–3.34 (2H, m), 3.62 (2H, s), 6.59 (2H, s), 7.16 (2H, dd, J=8.5, 8.5 Hz), 7.38 (2H, dd, J=5.7, 8.5 Hz), 8.14 (2H, d, J=8.4 Hz), 8.31 (2H, d, J=8.4 Hz), 9.12 m) Mass (m/z): 432 (M+ of free compound)

Elemental Analysis Calcd. for $C_{24}H_{24}FN_5O_2 \cdot C_4H_4O_4$: C 61.19, H 5.13, N 12.74 Found: C 61.16, H 5.02, N 12.65

(16) 5-(4-Acetylphenyl)-3-[[2-{1-(4-fluorobenzyl)piperidin-4-yl}ethyl]carbamoyl]-1,2,4-oxadiazole fumarate mp: 163°–164° C. IR (Nujol): 3275, 1690, 1260 cm$^{-1}$ NMR (DMSO-d$_6$, δ): 1.0–1.6 (5H, m), 1.6–1.8 (2H, m), 2.05–2.25 (2H, m), 2.67 (3H, s), 2.8–3.0 (2H, m), 3.2–3.4 (2H, m), 3.63 (2H, s), 6.59 (2H, s), 7.16 (2H, dd, J=8.8, 8.8 Hz), 7.38 (2H, dd, J=8.8, 5.8 Hz), 8.19 (2H, d, J=8.6 Hz), 8.29 (2H, d, J=8.6 Hz), 9.11 (1H, t, J=5.8 Hz)

(17) 3-[[2-{1-(4-Fluorobenzyl)piperidin-4-yl}ethyl]carbamoyl]-5-(4-mesylphenyl)-1,2,4-oxadiazole mp: 174°–175° C. IR (Nujol): 3350, 1665, 1140, 960, 780 cm$^{-1}$ NMR (DMSO-d$_6$, δ): 1.0–1.4 (3H, m), 1.4–1.6 (2H, m), 1.6–1.75 (2H, m), 1.8–2.0 (2H, m), 2.7–2.85 (2H, m), 3.2–3.4 (2H, m), 3.41 (2H, s), 7.12 (2H, dd, J=8.8, 8.8 Hz), 7.31 (2H, dd, J=8.8, 5.8 Hz), 8.21 (2H, d, J=8.6 Hz), 8.40 (2H, d, J=8.6 Hz), 9.13 (1H, t, J=5.8 Hz)

(18) 3-[[2-{1-(4-Fluorobenzyl)piperidin-4-yl}ethyl]carbamoyl]-5-(4-methylsulfinylphenyl)-1,2,4-oxadiazole fumarate mp: 178°–180° C. IR (Nujol): 3320, 1670, 1225 cm$^{-1}$ NMR (DMSO-d$_6$, δ): 1.1–1.6 (5H, m), 1.6–1.8 (2H, m), 2.0–2.2 (2H, m), 2.85 (3H, s), 2.8–3.0 (2H, m), 3.2–3.4 (2H, m), 3.59 (2H, s), 6.59 (2H, s), 7.16 (2H, dd, J=8.9, 8.9 Hz), 7.36 (2H, dd, J=8.9, 5.8 Hz), 7.97 (2H, d, J=8.4 Hz), 8.33 (2H, d, J=8.4 Hz), 9.10 (1H, t, J=5.8 Hz)

Elemental Analysis Calcd. for $C_{28}H_{31}FN_4O_7S$: C 57.32, H 5.32, N 9.55 Found: C 57.39, H 5.40, N 9.50

(19) 3-[[2-{1-(4-Fluorobenzyl)piperidin-4-yl}ethyl]carbamoyl]-5-(4-methylthiophenyl)-1,2,4-oxadiazole fumarate mp: 194°–195° C. (dec.) IR (Nujol): 3275, 1670, 1600, 980 cm$^{-1}$ NMR (DMSO-d$_6$, δ): 1.1–1.6 (5H, m), 1.6–1.8

(2H, m), 2.0–2.2 (2H, m), 2.58 (3H, s), 2.8–3.0 (2H, m), 3.3–3.4 (2H, m), 3.62 (2H, s), 6.59 (2H, s), 7.16 (2H, dd, J=8.8, 8.8 Hz), 7.37 (2H, dd, J=8.8, 5.7 Hz), 7.51 (2H, d, J=8.6 Hz), 8.05 (2H, d, J=8.6 Hz), 9.04 (1H, d, J=5.8 Hz)

(20) 3-[[2-{1-(4-Fluorobenzyl)piperidin-4-yl}ethyl]carbamoyl]-5-(4-trifluoromethylphenyl)-1,2,4-oxadiazole fumarate mp: 192°–194° C. IR (Nujol): 3300, 1700, 1670 cm$^{-1}$ NMR (DMSO-d$_6$, δ): 1.22–1.48 (5H, m), 1.72–1.77 (2H, m), 2.15–2.25 (2H, m), 2.90–2.96 (2H, m), 3.32–3.35 (2H, m), 3.69 (2H, s), 6.60 (2H, s), 7.13–7.22 (2H, m), 7.37–7.44 (2H, m), 8.05 (2H, d, J=8.3 Hz), 8.35 (2H, d, J=8.3 Hz), 9.11–9.15 (1H, m) Mass (m/z): 477 (M$^+$ of free compound+1)

(21) 3-[[2-{1-(4-Fluorobenzyl)piperidin-4-yl}ethyl]carbamoyl]-5-(2-cyanothiophen-5-yl]-1,2,4-oxadiazole fumarate NMR (DMSO-d$_6$, δ): 1.40–1.67 (7H, m), 2.00–2.15 (2H, m), 2.82–2.88 (2H, m), 3.32–3.40 (2H, m), 3.56 (2H, s), 6.58 (2H, s), 7.11–7.19 (2H, m), 7.30–7.38 (2H, m), 8.19 (2H, s), 9.10–9.16 (1H, m) Mass (m/z): 440 (M$^+$ of free compound+1)

(22) 3-[[2-{1-(4-Fluorobenzyl)piperidin-4-yl}ethyl]carbamoyl]-5-[(E)-2-(4-nitrophenyl)vinyl]-1,2,4-oxadiazole fumarate mp: 195°–198° C. (dec.) IR (Nujol): 3325, 1680, 1230 cm$^{-1}$ NMR (DMSO-d$_6$, δ): 1.0–1.6 (5H, m), 1.6–1.8 (2H, m), 1.9–2.1 (2H, m), 2.7–2.9 (2H, m), 3.2–3.4 (2H, m), 3.54 (2H, s), 6.60 (2H, s), 7.15 (2H, dd, J=8.7, 8.7 Hz), 7.36 (2H, dd, J=5.7, 8.7 Hz), 7.67 (1H, d, J=16.4 Hz), 8.07 (1H, d, J=16.4 Hz), 8.12 (2H, d, J=8.8 Hz), 8.30 (2H, d, J=8.8 Hz), 9.03 (1H, t, J=5.8 Hz)

(23) 3-[{2-(1-Methylpiperidin-4-yl)ethyl}carbamoyl]-5-(4-nitrophenyl)-1,2,4-oxadiazole fumarate mp: 195°–198° C. (dec.) IR (Nujol): 3320, 1700, 1680 cm$^{-1}$ NMR (DMSO-d$_6$, δ): 1.40–1.55 (5H, m), 1.82–1.87 (2H, m), 2.52 (3H, s), 2.57–2.72 (2H, m), 3.20–3.46 (4H, m), 6.53 (2H, s), 8.40 (2H, d, J=9.0 Hz), 8.49 (2H, d, J=9.0 Hz), 9.17–9.22 (1H, m)

Elemental Analysis Calcd. for C$_{17}$H$_{21}$N$_5$O$_4$·C$_4$H$_4$O$_4$: C 53.05, H 5.29, N 14.72 Found: C 52.85, H5.33, N 14.54

(24) 3-[[2-{1-(4-Fluorobenzyl)piperidin-4-yl}ethyl]carbamoyl]-5-[(E)-2-(4-cyanophenyl)vinyl]-1,2,4-oxadiazole fumarate mp: 220°–221° C. IR (Nujol): 3300, 2220, 1710, 1680, 1640 cm$^{-1}$ NMR (DMSO-d$_6$, δ): 1.18–1.49 (5H, m), 1.69–1.75 (2H, m), 2.07–2.18 (2H, m), 2.87–2.92 (2H, m), 3.29–3.32 (2H, m), 3.62 (2H, s), 6.59 (2H, s), 7.16 (2H, dd, J=8.8, 8.8 Hz), 7.37 (2H, dd, J=5.7, 8.8 Hz), 7.61 (1H, d, J=16.4 Hz), 7.95 (2H, d, J=8.5 Hz), 8.02 (1H, d, J=16.4 Hz), 8.05 (2H, d, J=8.5 Hz), 8.99–9.05 (1H, m)

(25) 2-[[2-{1-(4-Fluorobenzyl)piperidin-4-yl}ethyl]carbamoyl]-5-(4-cyanophenyl)-1,3,4-oxadiazole fumarate mp: 164°–165° C. IR (Nujol): 3300, 2225, 1685 cm$^{-1}$ NMR (DMSO-d$_6$, δ): 1.1–1.6 (5H, m), 1.6–1.8 (2H, m), 2.0–2.2 (2H, m), 2.8–2.95 (2H, m), 3.3–3.4 (2H, m), 3.58 (2H, s), 6.58 (2H, s), 7.15 (2H, dd, J=8.8, 8.8 Hz), 7.36 (2H, dd, J=8.8, 5.8 Hz), 8.11 (2H, d, J=8.6 Hz), 8.24 (2H, d, J=8.6 Hz), 9.40 (1H, t, J=5.8 Hz)

(26) 2-[[2-{1-(4-Fluorobenzyl)piperidin-4-yl}ethyl]carbamoyl]-5-(4-nitrophenyl)-1,3,4-oxadiazole fumarate mp: 191°–19 2° C. (dec.) IR (Nujol): 3300, 1690, 1340 cm$^{-1}$ NMR (DMSO-d$_6$, δ): 1.1–1.6 (5H, m), 1.6–1.8 (2H, m), 2.0–2.2 (2H, m), 2.8–3.0 (2H, m), 3.3–3.5 (2H, m), 3.62 (2H, s), 6.59 (2H, s), 7.16 (2H, dd, J=8.8 Hz), 7.37 (2H, dd, J=8.8, 5.9 Hz), 8.34 (2H, d, J=8.9 Hz), 8.46 (2H, d, J=8.9 Hz), 9.43 (1H, t, J=5.8 Hz)

(27) 2-[2-{1-(4-Fluorobenzyl)piperidin-4-yl}ethyl]carbamoyl-5-(mesylphenyl)-1,3,4-oxadiazole mp: 174°–175° C. IR (Nujol): 3350, 1680, 1155 cm$^{-1}$ NMR (DMSO-d$_6$, δ): 1.0–1.4 (3H, m), 1.4–1.6 (2H, m), 1.6–1.8 (2H, m), 1.8–2.0 (2H, m), 2.7–2.9 (2H, m), 3.33 (3H, s), 3.2–3.4 (2H, m), 3.42 (2H, s), 7.12 (2H, dd, J=8.8, 8.8 Hz), 7.32 (2H, dd, J=5.8, 8.8 Hz), 8.18 (2H, d, J=8.6 Hz), 8.33 (2H, d, J=8.6 Hz), 9.41 (1H, t, J=5.8 Hz)

(28) 5-[[2-{1-(4-Fluorobenzyl)piperidin-4-yl}ethyl]carbamoyl]-3-(4-nitrophenyl)-1,2,4-oxadiazole fumarate mp: 229°–231° C. (dec.) IR (Nujol): 1680, 970 cm$^{-1}$ NMR (DMSO-d$_6$, δ): 1.1–1.6 (5H, m), 1.6–1.8 (2H, m), 2.0–2.2 (2H, m), 2.8–3.0 (2H, m), 3.3–3.45 (2H, m), 3.59 (2H, s), 6.59 (2H, s), 7.16 (2H, dd, J=8.7 Hz), 7.37 (2H, dd, J=8.7, 5.8 Hz), 8.32 (2H, dd, J=7.0, 2.2 Hz), 8.46 (2H, dd, J=7.0, 2.2 Hz), 9.54 (1H, t, J=5.8 Hz)

(29) 3-[[2-(1-tert-Butoxycarbonylpiperidin-4-yl)ethyl]carbamoyl]-5-(4-nitrophenyl)-1,2,4-oxadiazole mp: 139°–141° C. IR (Nujol): 3380, 3300, 1740, 1680, 1600 cm$^{-1}$ NMR (DMSO-d$_6$, δ): 0.97–1.18 (3H, m), 1.39 (9H, s), 1.47–1.51 (2H, m), 1.66–1.72 (2H, m), 2.62–2.74 (2H, m), 3.32–3.36 (2H, m), 3.89–3.95 (2H, m), 8.40 (2H, d, J=9.1 Hz), 8.48 (2H, d, J=9.1 Hz), 9.15 (1H, t, J=5.8Hz)

(30) 3-[{2-(4-Pyridyl)ethyl}carbamoyl]-5-(4-cyanophenyl)-1,2,4-oxadiazole mp: 218°–220° C. IR (Nujol): 2220, 1680, 1600 cm$^{-1}$ NMR (DMSO-d$_6$, δ): 2.91 (2H, t, J=7.1 Hz), 3.55–3.65 (2H, m), 7.29 (2H, dd, J=1.5, 6.0 Hz), 8.15 (2H, d, J=8.6 Hz), 8.29 (2H, d, J=8.6 Hz), 8.48 (2H, dd, J=1.5, 6.0 Hz), 9.24 (1H, t, J=5.6 Hz) Mass (m/z): 319 (M$^+$)

(31) 3-[{2-(4-Pyridyl)ethyl}carbamoyl]-5-(4-nitrophenyl)-1,2,4-oxadiazole mp: 208°–209° C. IR (Nujol): 1680, 1600 cm$^{-1}$ NMR (DMSO-d$_6$, δ): 2.93 (2H, t, J=7.1 Hz), 3.60 (2H, m), 7.30 (2H, dd, J=1.4, 6.0 Hz), 8.37–8.50 (6H, m), 9.27 (1H, t, J=5.7 Hz)

EXAMPLE 15

The mixture of 2-acetoxy-5-(1-benzylpiperidin-4-yl)-1-(4-nitrobenzoyloxyimino)pentylamine (1.5 g) and molecular sieves 4A (7.5 g) in dioxane (50 ml) was refluxed for 2 hours. After molecular sieves were removed by filtration, the filtrate was evaporated in vacuo. The residue was chromatographed on silica eluting with 3% methanol in chloroform to give 3-[1-acetoxy-4-(1-benzylpiperidin-4-yl)butyl]-5-(4-nitrophenyl)-1,2,4-oxadiazole (0.63 g, 43.6%). The compound (74 mg) was dissolved in a solution of fumaric acid (18 mg) in ethanol to give 3-[1-acetoxy-4-(1-benzylpiperidin-4-yl)butyl]-5-(4-nitrophenyl)-1,2,4-oxadiazole fumarate (80 mg).

mp: 108°–110° C. IR (Nujol): 1750, 1710, 1660 cm$^{-1}$ NMR (DMSO-d$_6$, δ): 1.13–1.22 (7H, m), 1.60–1.65 (2H, m), 1.94–2.02 (2H, m), 2.08–2.10 (2H, m), 2.11 (3H, s), 2.84–2.90 (2H, m), 3.59 (2H, s), 5.91 (1H, t, J=6.7 Hz), 6.59 (2H, s), 7.30–7.32 (5H, m), 8.35 (2H, d, J=9.1 Hz), 8.44 (2H, d, J=9.1 Hz) Mass (m/z): 477 (M$^+$ of free compound−1)

EXAMPLE 16

The following compound was obtained according to a similar manner to that of Example 15.

3-{4-(1-Benzylpiperidin-4-yl)butyl}-5-(4-nitrophenyl)-1,2,4-oxadiazole fumarate mp: 157°–158° C. IR (Nujol): 1700, 1650 cm$^{-1}$ NMR (DMSO-d$_6$, δ): 1.20–1.40 (7H, m), 1.65–1.75 (4H, m), 2.30–2.40, (2H, m), 2.75–2.82 (2H, m), 2.90–3.05 (2H, m), 3.90–3.95 (2H, m), 6.60 (2H, s), 7.25–7.40 (5H, m), 8.36–8.42 (4H, br) Mass (m/z): 420 (M$^+$ of free compound)

EXAMPLE 17

The following compound was obtained according to a similar manner to that of Example 13.

3-[{2-(Piperidin-4-yl)ethyl}carbamoyl]-5-(4-nitrophenyl)-1,2,4-oxadiazole hydrochloride mp: 238°–240° C. (dec.) IR (Nujol): 3500, 3450, 3270, 1690, 1650 cm$^{-1}$ NMR (DMSO-d$_6$, δ): 1.34–1.60 (5H, m), 1.83–1.89 (2H, m), 2.78–2.83 (2H, m), 3.20–3.41 (4H, m), 8.40 (2H, d, J=8.9 Hz), 8.49 (2H, d, J=8.9 Hz), 8.92–8.96 (1H, br), 9.08–9.12 (1H, br), 9.18–9.23 (1H, m) Mass (m/z): 344 (M$^+$ of free compound−1)

EXAMPLE 18

(1) To a suspension of 3-[[2-{1-(4-fluorobenzyl)-4pyridinio}ethyl]carbamoyl]-5-(4-cyanophenyl)-1,2,4 -oxadiazole iodide (0.6 g) in methanol (5 ml)—tetrahydrofuran (7 ml) was added sodium borohydride (41 mg) at 0° C. under stirring. After stirring for 1 hour at ambient temperature, the mixture was poured into water and extracted with ethyl acetate. The extract was washed with water and brine, dried over magnesium sulfate and evaporated in vacuo. The residue was chromatographed on silica eluting with 3% methanol in chloroform and the fractions containing the object compound were evaporated in vacuo. The residue was dissolved in a solution of fumaric acid (106 mg) in ethanol (5 ml) to give 3-[[2-{1-(4-fluorobenzyl)-1,2,3,6-tetrahydropyridin-4-yl}ethyl]carbamoyl]-5-(4-cyanophenyl)-1,2,4-oxadiazole fumarate (0.35 g).

mp: 209°–211° C. IR (Nujol): 3230, 2230, 1710, 1670, 1600 cm$^{-1}$ NMR (DMSO-d$_6$, δ): 2.15–2.28 (4H, m), 2.65–2.71 (2H, m), 2.97–3.01 (2H, m), 3.37–3.50 (2H, m), 3.69 (2H, s), 5.40–5.43 (1H, br), 6.61 (2H, s), 7.16 (2H, dd, J=8.8, 8.8 Hz), 7.40 (2H, dd, J=5.7, 8.8 Hz), 8.15 (2H, d, J=8.6 Hz), 8.30 (2H, d, J=8.6 Hz), 9.06–9.12 (1H, m) Mass (m/z): 432 (M$^+$ of free compound+1)

The following compounds were obtained according to a similar manner to that of Example 18-(1).

(2) 3-[{2-(1-Benzyl-1,2,3,6-tetrahydropyridin-4-yl)ethyl}carbamoyl]-5-(4-nitrophenyl)-1,2,4-oxadiazole fumarate mp: 188°–189° C. (dec.) IR (Nujol): 3200, 1700, 1680 cm$^{-1}$ NMR (DMSO-d$_6$, δ): 2.09–2.15 (2H, br), 2.21–2.28 (2H, m), 2.60–2.66 (2H, m), 2.91–2.97 (2H, br), 3.35–3.50 (2H, m), 3.64 (2H, s), 5.39–5.43 (1H, br), 6.59 (2H, s), 7.26–7.35 (5H, m), 8.39 (2H, d, J=9.0 Hz), 8.47 (2H, d, J=9.0 Hz), 9.09–9.15 (1H, m) Mass (m/z): 434 (M$^+$ of free compound+1)

(3) 3-[[2-{1-(4-Fluorobenzyl)-1,2,3,6-tetrahydropyridin-4-yl}ethyl]carbamoyl]-5-(4-nitrophenyl)-1,2,4-oxadiazole fumarate mp: 191°–193° C. (dec.) IR (Nujol): 3230, 1700, 1670 cm$^{-1}$ NMR (DMSO-d$_6$, δ): 2.11–2.17 (2H, br), 2.22–2.28 (2H, m), 2.63–2.68 (2H, m), 2.95–2.99 (2H, m), 3.39–3.50 (2H, m), 3.67 (2H, s), 5.40–5.44 (1H, br), 6.60 (2H, s), 7.15 (2H, dd, J=8.8, 8.8 Hz), 7.38 (2H, dd, J=5.7, 8.8 Hz), 8.39 (2H, d, J=8.9 Hz), 8.48 (2H, d, J=8.9 Hz), 9.09–9.15 (1H, m) Mass (m/z): 452 (M$^+$ of free compound+1)

Elemental Analysis Calcd. for C$_{23}$H$_{22}$FN$_5$O$_4$·C$_4$H$_4$O$_4$: C 57.14, H 4.61, N 12.34 Found: C 57.23, H 4.63, N 12.30

(4) 3-[{2-(1-Benzyl-1,2,3,6-tetrahydropyridin-4-yl)ethyl}carbamoyl]-5-(4-cyanophenyl)-1,2,4-oxadiazole fumarate mp: 216°–217° C. IR (Nujol): 3240, 2220, 1700, 1670 cm$^{-1}$ NMR (DMSO-d$_6$, δ): 2.11–2.17 (2H, br), 2.21–2.28 (2H, m), 2.64–2.70 (2H, m), 2.97–3.02 (2H, br), 3.35–3.47 (2H, m), 3.69 (2H, s), 5.39–5.43 (1H, br), 6.60 (2H, s), 7.28–7.36 (5H, m), 8.14 (2H, d, J=8.6 Hz), 8.31 (2H, d, J=8.6 Hz), 9.06–9.12 (1H, m) Mass (m/z): 414 (M$^+$ of free compound+1)

Elemental Analysis Calcd. for C$_{24}$H$_{23}$N$_5$O$_2$·C$_4$H$_4$O$_4$: C 63.50, H 5.13, N 13.22 Found: C 63.46, H 5.17, N 13.09

EXAMPLE 19

A solution of 4N hydrogen chloride in ethyl acetate (0.56 ml) was added to a solution of 3-[[2-{1-(4-fluorobenzyl)piperidin-4-yl}ethyl]carbamoyl]-5-(4-cyanophenyl)-1,2,4-oxadiazole (0.8 g) in ethyl acetate (20 ml) under ice cooling. The resulting precipitates were filtered off, washed with diethyl ether, and dried in vacuo to give 3-[[2-{1-(4-fluorobenzyl)piperidin-4-yl}ethyl]carbamoyl]-5-(4-cyanophenyl)-1,2,4-oxadiazole hydrochloride (0.75 g).

mp: 245°–247° C. IR (Nujol): 3230, 1680 cm$^{-1}$ NMR (DMSO-d$_6$, δ): 1.50–1.53 (5H, m), 1.87–1.99 (2H, m), 2.81–2.85 (2H, m), 3.26–3.37 (4H, m), 4.24–4.36 (2H, m), 7.29 (2H, dd, J=8.8, 8.8 Hz), 7.72 (2H, dd, J=5.5, 8.8 Hz), 8.15 (2H, d, J=8.6 Hz), 8.31 (2H, d, J=8.6 Hz), 9.15–9.21 (1H, m) Mass (m/z): 433 (M$^+$ of free compound)

EXAMPLE 20

To a solution of 3-[1-acetoxy-4-(1-benzylpiperidin-4-yl)butyl]-5-(4-nitrophenyl)-1,2,4-oxadiazole (0.5 g) in methanol (10 ml) was added 4N an aqueous sodium hydroxide solution (0.5 ml) at 0° C. After stirring at 0° C. for 2 hours, ice water was added to the mixture and the precipitates were filtrated to give 3-[1-hydroxy-4-(1-benzylpiperidin-4-yl)butyl]-5-(4-nitrophenyl)-1,2,4-oxadiazole (0.44 g). The compound (100 mg) was dissolved in a solution of fumaric acid (27 mg) in ethanol to give 3-[1-hydroxy-4-(1-benzylpiperidin-4-yl)butyl]-5-(4-nitrophenyl)-1,2,4-oxadiazole fumarate (0.1 g).

mp: 78°–81° C. (dec.) IR (Nujol): 3350, 1700, 1650 cm$^{-1}$ NMR (DMSO-d$_6$, δ): 1.20–1.40 (7H, m), 1.63–1.68 (2H, m), 1.79–1.83 (2H, m), 2.12–2.26 (2H, m), 2.91–2.96 (2H, m), 3.70 (2H, s), 4.77 (1H, t, J=6.7 Hz), 6.59 (2H, s), 7.10–7.35 (5H, m), 8.35 (2H, d, J=9.0 Hz), 8.45 (2H, d, J=9.0 Hz) Mass (m/z): 436 (M$^+$ of free compound)

EXAMPLE 21

The mixture of 3-[1-hydroxy-4-(1-benzylpiperidin-4-yl)butyl]-5-(4-nitrophenyl)-1,2,4-oxadiazole (0.28 g), N,N-dicyclohexylcarbodiimide (0.66 g) and o-phosphoric acid (0.31 g) in dimethyl sulfoxide (5 ml) was stirred overnight at ambient temperature and extracted with ethyl acetate. The extract was washed with water and brine, dried over magnesium sulfate and evaporated in vacuo. The residue was chromatographed on silica eluting with 3% methanol in chloroform to give 3-[1-oxo-4-(1-benzylpiperidin-4-yl)butyl]-5-(4-nitrophenyl)-1,2,4-oxadiazole as an oil (0.21 g). The oil was dissolved in a solution of fumaric acid (48 mg)

in ethanol and the crystals were filtered off to give 3-[1-oxo-4-(1-benzylpiperidin-4-yl)butyl]-5-(4-nitrophenyl)-1,2,4-oxadiazole fumarate (0.18 g).

mp: 159°–161° C. IR (Nujol): 1710, 1650 cm$^{-1}$ NMR (DMSO-d$_6$, δ): 1.25–1.35 (5H, m), 1.71–1.76 (4H, m), 2.32–2.44 (2H, m), 3.00–3.15 (4H, m), 3.83 (2H, s), 6.60 (2H, s), 7.38–7.41, (5H, m), 8.41 (2H, d, J=9.1 Hz), 8.47 (2H, d, J=9.1 Hz) Mass (m/z): 434 (M$^+$ of free compound)

Elemental Analysis Calcd. for $C_{24}H_{26}N_4O_4 \cdot C_4H_4O_4$: C 61.08, H 5.49, N 10.17 Found: C 60.87, H 5.47, N 10.05

EXAMPLE 22

A mixture of paraformaldehyde (70 mg), copper(I) chloride (10 mg) and pyrrolidine (0.1 ml) in dioxane (2 ml) was stirred at ambient temperature. After stirring for 30 minutes, a solution of 3-{(2-propynyl)carbamoyl}-5-(4-nitrophenyl)-1,2,4-oxadiazole (300 mg) in dioxane (3 ml) was added dropwise to the mixture and stirred overnight. The resulting precipitates were removed out by filtration and the filtrate was evaporated in vacuo. The residue was chromatographed on silica eluting with 3% methanol in chloroform and the fractions containing the object compound were evaporated in vacuo. The residue was dissolved in ethanol and 4N hydrogen chloride in ethanol was added, and the precipitates was filtered off to give 3-[{4-(pyrrolidin-1-yl)-2-butynyl]carbamoyl]-5-(4-nitrophenyl)-1,2,4-oxadiazole hydrochloride (0.2 g).

mp: 214°–216° C. (dec.) IR (Nujol): 3170, 2550, 2450, 1695 cm$^{-1}$ NMR (DMSO-d$_6$, δ): 1.94–1.97 (4H, m), 3.18–3.56 (4H, m), 4.10 (2H, s), 4.20 (2H, d, J=5.4 Hz), 8.40 (2H, d, J=9.1 Hz), 8.50 (2H, d, J=9.1 Hz), 9.73 (1H, t, J=5.4 Hz) Mass (m/z): 355 (M$^+$ of free compound)

EXAMPLE 23

(1) To a mixture of 3-{(E)-2-carboxyvinyl}-5-(4-cyanophenyl)-1,2,4-oxadiazole (0.25 g), 2-(1-benzylpiperidin-4-yl)ethylamine (0.23 g) and 1-hydroxybenzotriazole hydrate (0.16 g) in N,N-dimethylformamide (5 ml) was added 1-ethyl-3-(3-dimethylaminopropyl)carbodiimide (0.20 ml) at 5° C. After stirring for 1 hour at ambient temperature, the mixture was poured into water and extracted with ethyl acetate. The extract was washed with water and brine, dried over magnesium sulfate and evaporated in vacuo. The residue was chromatographed on silica eluting with 2% methanol in chloroform and the fractions containing the object compound were evaporated in vacuo. The residue was dissolved in a solution of fumaric acid (71 mg) in ethanol to give 3-[(E)-2-[{2-(1-benzylpiperidin-4-yl)ethyl}carbamoyl]vinyl]-5-(4-cyanophenyl)-1,2,4-oxadiazole fumarate (0.32 g).

mp: 231°–232° C. IR (Nujol): 3240, 2220, 1700, 1670, 1640 cm$^{-1}$ NMR (DMSO-d$_6$, δ): 1.22–1.50 (5H, m), 1.67–1.73 (2H, m), 2.11–2.22 (2H, m), 2.90–2.96 (2H, m), 3.20–3.30 (2H, m), 3.66 (2H, s), 6.59 (2H, s), 7.20 (1H, d, J=15.5 Hz), 7.28–7.39 (6H, m), 8.13 (2H, d, J=8.6 Hz), 8.28 (2H, d, J=8.6 Hz), 8.53–8.56 (1H, m) Mass (m/z): 442 (M$^+$ of free compound+1)

The following compounds were obtained according to a similar manner to that of Example 23-(1).

(2) 3-[(E)-2-{(1-Benzylpiperidin-4-yl)carbamoyl}vinyl]-5-(4-nitrophenyl)-1,2,4-oxadiazole fumarate mp: 266°–268° C. IR (Nujol): 3240, 1700, 1670, 1650 cm$^{-1}$ NMR (DMSO-d$_6$, δ): 1.44–1.56 (2H, m), 1.80–1.86 (2H, m), 2.14–2.25 (2H, m), 2.82–2.87 (2H, m), 3.57 (2H, s), 3.65–3.75 (1H, m), 6.61 (2H, s), 7.24 (1H, d, J=15.5 Hz), 7.33–7.40 (6H, m), 8.36 (2H, d, J=9.0 Hz), 8.48 (2H, d, J=9.0 Hz), 8.55 (1H, d, J=7.6 Hz) Mass (m/z): 434 (M$^+$ of free compound+1)

Elemental Analysis Calcd. for $C_{23}H_{23}N_5O_4 \cdot C_4H_4O_4$: C 59.01, H 4.95, N 12.74 Found: C 58.80, H 4.93, N 12.67

(3) 3-[(E)-2-[{2-(1-Benzylpiperidin-4-yl)ethyl}carbamoyl]vinyl]-5-(4-nitrophenyl)-1,2,4-oxadiazole fumarate mp: 221°–223° C. IR (Nujol): 3260, 1700, 1660, 1630 cm$^{-1}$ NMR (DMSO-d$_6$, δ): 1.26–1.42 (5H, m), 1.68–1.74 (2H, m), 2.12–2.23 (2H, m), 2.91–2.96 (2H, m), 3.22–3.25 (2H, m), 3.67 (2H, s), 6.59 (2H, 7.22 (1H, d, J=15.6 Hz), 7.32–7.40 (6H, m), 8.37 (2H, d, J=9.0 Hz), 8.47 (2H, d, J=9.0 Hz), 8.54–8.58 (1H, m) Mass (m/z): 462 (M$^+$ of free compound+1)

(4) 3-[(E)-2-[[2-{1-(4-Fluorohehzylpiperidin-4-yl}ethyl]carbamoyl]vinyl]-5-(4-nitrophenyl)-1,2,4-oxadiazole fumarate mp: 229°–230° C. IR (Nujol): 3250, 1700, 1660, 1630 cm$^{-1}$ NMR (DMSO-d$_6$, δ): 1.25–1.42 (5H, m), 1.68–1.74 (2H, m), 2.11–2.22 (2H, m), 2.89–2.95 (2H, m), 3.23–3.25 (2H, m), 3.66 (2H, s), 6.59 (2H, s), 7.17 (2H, dd, J=8.8, 8.8 Hz), 7.21 (1H, d, J=16.9 Hz), 7.36 (1H, d, J=16.9 Hz), 7.39 (2H, dd, J=5.7, 8.8 Hz), 8.36 (2H, d, J=9.0 Hz), 8.47 (2H, d, J=9.0 Hz), 8.52–8.58 (1H, m) Mass (m/z): 480 (M$^+$ of free compound+1)

Elemental Analysis Calcd. for $C_{25}H_{26}FN_5O_4 \cdot C_4H_4O_4$: C 58.48, H 5.07, N 11.75 Found: C 58.21, H 5.19, N 11.61

(5) 3-[(E)-2-[[2-{1-(4-Fluorobenzylpiperidin-4-yl}ethyl]carbamoyl]vinyl]-5-(4-cyanophenyl)-1,2,4-oxadiazole fumarate mp: 238°–240° C. IR (Nujol): 3260, 2230, 1700, 1670, 1630 cm$^{-1}$ NMR DMSO-d$_6$, δ): 1.24–1.41 (5H, m), 1.67–1.73 (2H, m), 2.07–2.18 (2H, m), 2.87–2.92 (2H, m), 3.22–3.25 (2H, m), 3.62 (2H, s), 6.59 (2H, s), 7.16 (2H, dd, J=8.7, 8.7 Hz), 7.20 (1H, d, J=15.3 Hz), 7.35 (1H, d, J=15.3 Hz), 7.35 (2H, dd, J=5.7, 8.7 Hz), 8.13 (2H, d, J=8.5 Hz), 8.28 (2H, d, J=8.5 Hz), 8.52–8.57 (1H, m) Mass (m/z): 460 (M$^+$ of free compound+1)

Elemental Analysis Calcd. for $C_{26}H_{26}FN_5O_2 \cdot C_4H_4O_4$: C 62.60, H 5.25, N 12.16 Found: C 62.45, H 5.20, N 12.08

We claim:

1. A compound of the the formula:

$R^1$-Q-Z-X-A-M wherein

Q is oxadiazolediyl,

Z is bond or vinyl,

A is bond, lower alkylene or lower alkynylene wherein $R^1$ is lower alkyl; unsaturated 5 or 6-membered heteromonocyclic group containing 1 to 4 nitrogen atom(s), unsaturated 5 or 6-membered heteromonocyclic group containing 1 to 2 sulfur atom(s) or saturated heterobicyclic group of the formula:

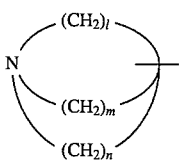

(wherein l, m and n are each integer of 1 to 3), each of which may have 1 to 2 substituent(s) selected from the group consisting of lower alkyl, lower alkenyl, lower alkynyl, lower alkoxy, lower alkylthio, lower alkylsulfinyl, cyano, nitro, mono(or di or tri)halo(lower)alkyl and acyl;

phenyl which may have 1 to 2 substituent(s) selected from the group consisting of lower alkyl, lower alkoxy, nitro, halogen, mono(or di or tri)halo(lower)alkyl, lower alkylthio, lower alkylsulfinyl, cyano, lower alkylsulfonyl and lower alkanoyl;

phenyl(lower)alkyl which may have 1 to 2 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl; or phenyl(lower)alkenyl which may have 1 to 2 substituent(s) selected from the group consisting of lower alkyl, lower alkoxy, nitro, mono(or di or tri)halo(lower)alkyl, cyano, lower alkylthio, lower alkylsulfinyl and lower alkylsulfonyl, X is a group of the formula:

(in which $R^4$ is hydrogen or lower alkyl), a group of the formula:

(in which $R^8$ is hydroxy or lower alkanoyloxy),

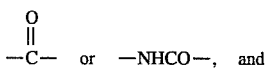

M is piperidyl, piperazinyl, or pyrrolidinyl, each of which may have one substituent selected from the group consisting of lower alkyl, acyl and phenyl(lower)alkyl which may have 1 to 2 substituent(s) selected from the group consisting of halogen, cyano, nitro, lower alkyl, lower alkoxy and lower alkylthio.

2. A compound of claim 1, wherein $R^1$ is lower alkyl; pyridyl, thienyl or quinuclidinyl, each of which may have cyano;

phenyl which may have a substituent selected from the group consisting of lower alkyl, lower alkoxy, nitro, halogen, mono(or di or tri)halo(lower)alkyl, lower alkylthio, lower alkylsulfinyl, cyano, lower alkylsulfonyl and lower alkanoyl;

phenyl(lower)alkyl which may have nitro; or phenyl(lower)alkenyl which may have cyano or nitro, and M is piperidyl, piperazinyl, or pyrrolidinyl, each of which may have one substituent selected from the group consisting of lower alkyl, lower alkoxycarbonyl and phenyl(lower)alkyl which may have a substituent selected from the group consisting of halogen, cyano, nitro, lower alkyl and lower alkoxy.

3. A compound of the formula:

$R^1$-Q-Z-X-A-M wherein $R^1$ is phenyl which may have a substituent selected from the group consisting of lower alkyl, lower alkoxy, nitro, halogen, mono(or di or tri)halo(lower)alkyl, lower alkylthio, lower alkylsulfinyl, cyano, lower alkylsulfonyl and lower alkanoyl, Q is

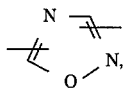

Z is bond,

X is

(in which $R^4$ is hydrogen),

A is lower alkylene, and

M is piperidyl which has phenyl(lower)alkyl which may have a substituent selected from the group consisting of halogen, cyano, nitro, lower alkyl and lower alkoxy.

4. A compound of claim 3, which is a compound of the formula:

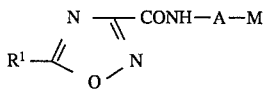

wherein $R^1$ is cyanophenyl,

A is lower alkylene, and

M is piperidyl having halophenyl(lower)alkyl.

5. A compound of claim 4, which is selected from the group consisting of:

3-[[2-{1-(4-Fluorobenzyl)piperidin-4-yl}ethyl]carbamoyl]-5-(4-cyanophenyl)-1,2,4-oxadiazole fumarate, 3-[[2-{1-(3-Fluorobenzyl)piperidin-4-yl}ethyl]carbamoyl]-5-(4-cyanophenyl)-1,2,4-oxadiazole fumarate, 3-[[2-{1-(2-Fluorobenzyl)piperidin-4-yl}ethyl]carbamoyl]-5-(4-cyanophenyl)-1,2,4-oxadiazole fumarate, 3-[[2-{1-(4-Chlorobenzyl)piperidin-4-yl}ethyl]carbamoyl]-5-(4-cyanophenyl)-1,2,4-oxadiazole fumarate and 3-[[2-{1-(4-Fluorobenzyl)piperidin-4-yl}ethyl]carbamoyl]-5-(4-cyanophenyl)-1,2,4-oxadiazole hydrochloride.

6. A pharmaceutical composition which comprises, as an active ingredient, a compound of claim 1 or a pharmaceutically acceptable salt thereof in admixture with pharmaceutically acceptable carriers.

7. A method for the prophylactic or therapeutic treatment of dementia which comprises administering a compound of claim 1 or a pharmaceutically acceptable salt thereof to human or animals.

* * * * *